(12) United States Patent
Arnold et al.

(10) Patent No.: US 6,395,733 B1
(45) Date of Patent: May 28, 2002

(54) HETEROCYCLIC RING-FUSED PYRIMIDINE DERIVATIVES

(75) Inventors: Lee Daniel Arnold, Westborough, MA (US); Mikel P. Moyer, Old Lane; Susan B. Sobolov-Jaynes, Ivoryton, both of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/423,510

(22) PCT Filed: Jun. 7, 1995

(86) PCT No.: PCT/US95/07881

§ 371 (c)(1),
(2), (4) Date: Nov. 9, 1999

(87) PCT Pub. No.: WO96/40142

PCT Pub. Date: Dec. 19, 1996

(51) Int. Cl.[7] ..................... C07D 487/04; A61K 31/519
(52) U.S. Cl. ................. 514/234.2; 514/234.5; 514/258; 544/117; 544/280
(58) Field of Search ................. 544/280, 117; 514/258, 234.2, 234.5

(56) References Cited

U.S. PATENT DOCUMENTS

| | | | |
|---|---|---|---|
| 4,012,513 A | 3/1977 | Birchall et al. | 424/251 |
| 5,041,542 A | 8/1991 | Robins et al. | 536/24 |
| 5,106,974 A | 4/1992 | Akimoto et al. | 544/280 |
| 5,378,700 A | 1/1995 | Sakuma et al. | 514/212 |
| 5,686,457 A * | 11/1997 | Traxler et al. | 514/258 |
| 5,864,033 A | 1/1999 | Browne et al. | 536/27.13 |
| 6,096,749 A * | 8/2000 | Traxler et al. | 514/258 |
| 6,140,317 A * | 10/2000 | Traxler et al. | 514/183 |
| 6,140,332 A * | 10/2000 | Traxler et al. | 514/258 |
| 6,180,636 B1 * | 1/2001 | Traxler et al. | 514/258 |

FOREIGN PATENT DOCUMENTS

| | | |
|---|---|---|
| DE | 3036390 * | 5/1982 |
| EP | 0075881 | 4/1983 |
| EP | 0089055 | 9/1983 |
| EP | 0160910 | 11/1985 |
| EP | 0260491 | 3/1988 |
| EP | 0475413 | 3/1992 |
| WO | 9413676 | 6/1994 |
| WO | 9417803 | 8/1994 |
| WO | 9501355 | 1/1995 |
| WO | 9519774 | 7/1995 |

OTHER PUBLICATIONS

Nishikawa, S. et al., Preparation and Structure–Activity Relationships of 4–Substituted Amino–2–methylpyrido[3,4–d]pyrimidines as Cytokinin Analogs, *J. Agric. Food Chem.* vol. 43, pp. 1034–1038 (1995).
Marquet et al., Chem. Abstract 76:126924, May 1972.*
Bisagni et al., Chem. Abstract 81:9617, Jul. 1974.*
Jorgensen et al., Phosphorous Pentoxide in Organic Synthesis., J. Het. Chem., vol. 22, No. 3, pp. 859–863, May 1985.*
Simone, Oncology: Introduction, Cecil Textbook of Medicine, 20th Edition, vol. 1, pp. 1004–1110, 1996.*

* cited by examiner

*Primary Examiner*—Richard L. Raymond
*Assistant Examiner*—Deepak Rao
(74) *Attorney, Agent, or Firm*—Peter C. Richardson; Paul H. Ginsburg; Jeffrey N. Myers

(57) ABSTRACT

The present invention relates to heterocyclic ring-fused pyrimidine derivatives of formula (I) or stereoisomers, pharmaceutically acceptable salts or prodrugs thereof, wherein Z and Y are as defined in the specification. Compounds of formula (I) are useful in the treatment of hyperproliferative diseases, such as cancers and acnes, in mammals:

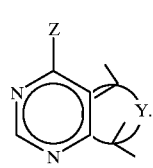

(I)

9 Claims, No Drawings

HETEROCYCLIC RING-FUSED PYRIMIDINE DERIVATIVES

This application is a 371 of PCT/US95/07881 filed Jun. 7, 1995.

BACKGROUND OF THE INVENTION

This invention relates to heterocyclic ring-fused pyrimidine derivatives and methods of using the same in the treatment of hyperproliferative diseases, such as cancers and acnes, in mammals.

Many of the current treatment regimes for cancer utilize compounds which inhibit DNA synthesis. Such compounds are toxic to cells generally but their toxic effect on the rapidly dividing tumor cells can be beneficial. Alterative approaches to anti-cancer agents which act by mechanisms other than the inhibition of DNA synthesis have been explored in order to enhance the selectivity of action against cancer cells.

It is known that a cell may become cancerous by virtue of the transformation of a portion of its DNA into an oncogene (i.e. a gene which, on activation, leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR) which possesses tyrosine kinase activity is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as a selective inhibitors of the growth of mammalian cancer cells. For example, erbstatin, a tyrosine kinase inhibitor selectively attenuates the growth in athymic nude mice of a transplanted human mammary carcinoma which expresses epidermal growth factor receptor tyrosine kinase (EGFR) but is without effect on the growth of another carcinoma which does not express the EGF receptor.

Various other compounds, such as styrene derivatives, have also been shown to possess tyrosine kinase inhibitory properties. More recently three European patent publications, namely EP 0 566 226 A1, EP 0 602 851 A1 and EP 0 520 722 A1 have disclosed that certain heteroaryl-fused pyrimidine derivatives possess anti-cancer properties which result from their tyrosine kinase inhibitory properties. Also PCT publication WO 92/20642 discloses bis-mono and bicyclic aryl and heteroaryl compounds as tyrosine kinase inhibitors.

European patent publication EP 0 496 617 A1 discloses certain pyrazolo[3,4-d]pyrimidines and pyrrolo[2,3-d]pyrimidines which possess adenosine kinase inhibitory properties.

European patent publication EP 0 475 413 A2 discloses certain carbocyclic nucleoside analogs as useful immunosuppressants.

European patent publication EP 0 414 386 A1 discloses certain pyrido[2,3-d]pyrimidines as fungicides, insecticides and miticides. The synthesis and antiallergic activity of 9-aryl-8-azaadenine derivatives is described in *II Farmco—Ed. Sc.*, vol 35, fasc. 4 p308–323 (1980).

Co-pending U.S. patent applications (U.S. Ser. Nos. 08/200,359 and 08/413,800) and PCT application docket no. PC8836A, assigned to the Assignee of this application, describe optionally substituted indolyl- and phenylamino quinazolines, respectively, which are useful in the treatment of hyperproliferative diseases involving receptor tyrosine kinases. In addition U.S. Pat. No. 4,012,513 discloses certain 1-(heterocyclic)-indol-3-yl-acetic acid derivatives that have anti-inflammatory, analgesic and antipyretic activity.

Although the anti-cancer compounds described above make a significant contribution to the art there is a continuing search in this field of art for improved anti-cancer pharmaceuticals.

SUMMARY OF THE INVENTION

This invention is directed to compounds of the Formula

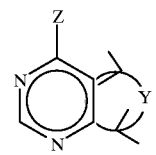

I and stereoisomers, pharmaceutically acceptable salts and prodrugs thereof, wherein Y together with the carbons to which it is attached form a 5 or 6 membered, optionally unsaturated or aromatic ring wherein said ring is optionally substituted with $(R^3)_p$ and/or $R^4$ groups and comprises one to three heteroatoms selected from S, O and N with the proviso that at least one of said hetero atoms is N;

Z is $NR^1R^2$ wherein $R^1$ is H and $R^2$ is phenyl substituted by $(R^5)_m$ or Q or $R^1R^2N$ is a group of the formula

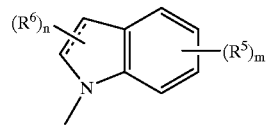

wherein the dotted line represents an optional double bond;
each $R^3$ is attached to a carbon atom in Y and is independently selected from
a. hydrogen, trifluoromethyl, halo, nitro, hydroxy, amino, cyano, $(C_1-C_4)$alkyl, $(C_1-C_4)$alkoxy, $(C_1-C_4)$alkoxycarbonyl, $(C_1-C_4)$alkanoyloxy, $(C_1-C_4)$alkanoylamino, carboxy, phenoxy, benzoyloxy, carbamoyl, mono-N- or di-N,N-di-$(C_1-C_4)$alkylcarbamoyl, mono-N- or di-N,N-$(C_1-C_4)$alkylamino, mono-N or di-N,N-(hydroxy$(C_2-C_4)$alkyl)amino, mono-N or di-N,N-$((C_1-C_4)$alkoxy$(C_2-C_4)$alkyl)amino, anilino, pyrrolidin-1-yl, piperidin-1-yl, morpholino, piperazin-1-yl, 4$(C_1-C_4)$alkylpiperazin-1-yl, pyridyl, pyrrolo, imidazolo, thiazolo, benzimidazolo, pyridonyl, $(C_{1-4})$alkylthio, phenylthio, or such groups substituted on $(C_1-C_4)$alkyl;

b. hydroxy($C_2$–$C_4$)alkoxy($C_1$–$C_4$)alkyl, ($C_1$–$C_4$) alkoxy-($C_2$–$C_4$)alkoxy-($C_1$–$C_4$)alkyl, hydroxy($C_2$–$C_4$)alkylthio($C_1$–$C_4$)alkyl, ($C_1$–$C_4$)alkoxy($C_2$–$C_4$)alkylthio($C_1$–$C_4$)alkyl, hydroxyamino, benzoylamino, mono-N or di- N,N-($C_1$–$C_4$)alkylcarbamoylmethylamino, carbamoylmethylamino, ($C_1$–$C_4$)alkoxycarbonylamino, ($C_1$–$C_4$)alkanoylamino, carboxymethylamino, ($C_1$–$C_4$)alkoxycarbonylmethylamino, ($C_1$–$C_4$)alkoxyamino, ($C_2$–$C_4$)alkanoyloxyamino, phenyl($C_1$–$C_4$)alkylamino, ($C_1$–$C_4$)alkylsulphonylamino, benzenesulphonamido, 3phenylureido, 2-oxopyrrolidin-1-yl, 2,5-dioxopyrrolidin-1-yl, ureido,($C_1$–$C_4$)alkoxy($C_1$–$C_4$)alkylcarbonylamino, ($C_1$–$C_4$)alkylsulfinyl,($C_1$–$C_4$)alkylsulfonyl, ($C_1$–$C_4$)alkoxy($C_2$–$C_4$)alkylthio, mono-, di- or trifluoromethyloxy, ($C_1$–$C_4$)alkylenedioxy, benzyloxy, guanidino, aminocarbonyl, mono-N- or di-N,N-($C_1$–$C_4$)alkylaminocarbonyl, phenyl($C_1$–$C_4$)alkoxy, carboxymethoxy, ($C_1$–$C_4$)alkoxycarbonylmethoxy, carbamoylmethoxy, mono-N or di-N,N-($C_1$–$C_4$)alkyl carbamoylmethoxy, mono-N- or di-N,N-(hydroxy($C_2$–$C_4$)alkyl)carboxamido, mono-N- or di-N,N-(($C_1$–$C_4$)alkoxy ($C_2$–$C_4$)alkyl)carboxamido or bis(($C_1$–$C_4$)alkanesulfonyl)amido; or c. ($C_2$–$C_4$)alkoxy, ($C_2$–$C_4$)alkylthio, ($C_2$–$C_4$)alkanoyloxy, ($C_2$–$C_4$)alkylamino, ($C_1$–$C_4$)alkyl($C_1$–$C_4$)alkylenedioxy, ($C_2$–$C_4$)alkanoylamino, ($C_2$–$C_4$)alkenyl, or ($C_2$–$C_4$)alkynyl; each such group substituted with amino, halo, hydroxy, ($C_2$–$C_4$)alkanoyloxy, ($C_1$–$C_4$)alkoxy, mono-N- or di-N,N-($C_1$–$C_4$)alkylamino, mono-N or di-N,N-(hydroxy($C_2$–$C_4$)alkyl)amino, mono-N or di-N,N-(($C_1$–$C_4$)alkoxy($C_2$–$C_4$)alkyl)amino, ($C_1$–$C_4$)alkanoylamino, phenoxy, anilino, imidazol-1-yl, phenylthio, piperidino, pyridyl, carboxy($C_1$–$C_4$)alkylthio ($C_1$–$C_4$)alkoxy, morpholino, piperazin-1-yl-, 4-($C_1$–$C_4$)alkylpiperazin-1-yl-, carboxy, ($C_1$–$C_4$)alkoxycarbonyl, carbamoyl, mono-N- or di-N,N-($C_1$–$C_4$)alkylcarbamoyl, carboxamido, mono-N- or di-N,N-($C_1$–$C_4$)alkylcarboxamido or mono-N- or di-N,N-(hydroxy($C_2$–$C_4$)alkyl)carboxamido; and any phenyl in an $R^3$ substituent is optionally mono- or di- substituted with halo, nitro, trifluoromethyl, hydroxy, ($C_1$–$C_4$)alkoxy, ($C_1$–$C_4$)alkyl, amino, mono-N-alkylamino, or N,N-dialkylamino;

$R^4$ is attached to a N-atom in Y and is independently selected from:
hydrogen, ($C_1$–$C_4$)alkyl, ($C_1$–$C_4$)alkoxycarbonyl, ($C_1$–$C_4$)alkanoyl, ($C_1$–$C_4$)alkylsulfonyl, arylsulfonyl, allyl; or a ($C_2$–$C_4$)alkyl, ($C_2$–$C_4$)alkanoyl, or ($C_2$–$C_4$)alkoxycarbonyl, ($C_2$–$C_4$)alkylsulfonyl, each such group substituted with amino, halo, hydroxy, ($C_2$–$C_4$)alkanoyloxy, ($C_1$–$C_4$)alkoxy, mono-N- or di-N,N-($C_1$–$C_4$)alkylamino, mono-N or di-N,N-(hydroxy($C_2$–$C_4$)alkyl)amino, mono-N or di-N,N-($C_1$–$C_4$)alkoxy($C_2$–$C_4$)alkyl)amino, ($C_1$–$C_4$)alkanoylamino, phenoxy, anilino, imidazol-1-yl, phenylthio, piperidino, morpholino, piperazin-1-yl-, 4-($C_1$–$C_4$)alkylpiperazin-1-yl-, phenyl, pyridyl, pyrrolo, imidazolo, thiazolo, benzimidazolo, pyridenyl, carboxy, ($C_1$–$C_4$)alkoxycarbonyl, carbamoyl, mono-N- or di-N,N-($C_1$–$C_4$)alkylcarbamoyl, carboxamido, mono-N- or di-N,N-($C_1$–$C_4$)alkylcarboxamido or mono-N- or di-N,N-(hydroxy($C_2$–$C_4$)alkyl)carboxamido; and any phenyl in an $R^4$ substituent is optionally mono- or di- substituted with halo, nitro, trifluoromethyl, hydroxy, ($C_1$–$C_4$)alkoxy, ($C_1$–$C_4$)alkyl, amino, mono-N-alkylamino, or N,N-dialkylamino; but specifically $R^4$ is not furanosyl, pyranosyl, or cyclopentyl;

each $R^5$ is independently selected from mono-, di- or tri-fluoromethyl, halo, nitro, hydroxy, amino, azido, isothiocyano, ($C_1$–$C_4$)alkyl, phenyl, thienyl, ($C_1$–$C_4$)alkoxy, benzyloxy, phenoxy, ($C_2$–$C_6$)alkenyl, ($C_2$–$C_6$)alkynyl ($C_1$–$C_4$)alkylenedioxy, cyano, benzoylamino, trifluoromethylcarbonylamino, ($C_1$–$C_4$)alkanoylamino, ($C_1$–$C_4$)alkanoyl, N-mono- or N,N-di-($C_1$–$C_4$)alkylamino, ($C_1$–$C_4$)alkylsulfonylamino, trifluoromethylsulfonylamino, ($C_1$–$C_4$)alkylthio, ($C_1$–$C_4$)alkylfinyl or ($C_1$–$C_4$)alkylsulfonyl, pyrrol-1-yl, piperidin-1-yl or pyrrolidin-1-yl, said phenyl, benzyloxy, phenoxy and benzoylamino optionally mono-substituted with halo, nitro, trifluoromethyl, hydroxy or ($C_1$–$C_4$)alkyl and said ($C_1$–$C_4$)alkylenedioxy is linked at both ends to adjacent carbons on the benzene moiety;

each $R^6$ is independently selected from hydroxy, amino, N-mono- or N,N-di-($C_1$–$C_4$)alkylamino, sulfo, or ($C_1$–$C_4$)alkoxy (provided that such groups are not attached to a ring carbon which is directly adjacent to the ring N-), or $R^6$ for each occurrence is independently carboxy, hydroxy($C_1$–$C_4$)alkyl, ($C_1$–$C_4$)alkoxy($C_1$–$C_4$)alkyl, amino($C_1$–$C_4$)alkyl, mono-N- or di-N,N-($C_1$–$C_4$)alkylamino($C_1$–$C_4$)alkyl, morpholino ($C_1$–$C_4$)alkyl, 4-($C_1$–$C_4$)alkyl-piperazin-1-yl($C_1$–$C_4$)alkyl, carboxy ($C_1$–$C_4$)alkyl, ($C_1$–$C_4$)alkoxycarbonyl, sulfo($C_1$–$C_4$)alkyl, pyridyl($C_1$–$C_4$)alkyl or ($C_1$–$C_4$)alkyl;

m is an integer from 1 to 3;

n is 0, 1 or 2;

p is 0 or an integer from 1–3;

with the proviso that when Y, In the direction shown by the arrow in formula I, is —$CR^3$=N—$CR^3$=$CR^3$—, p=0, m=1 and Z is substituted phenyl then $R^5$ is not 4-ethoxy, 4-methoxy, 4-trifluoromethoxy, 4-t-butyl or 4isopropyl;

Q is a 9- or 10-membered bicyclic heteroaryl cyclic moiety, or a hydrogenated derivative thereof, containing one or two nitrogen heteroatoms and optionally containing a further heteroatom selected from nitrogen, oxygen and sulphur, or Q is a 9- or 10-membered bicyclic aryl moiety, or a hydrogenated derivative thereof, which heterocyclic or aryl moiety, or hydrogenated derivatives thereof, may optionally bear one or two substituents selected from halogeno, hydroxy, oxo, amino, nitro, carbamoyl, ($C_1$–$C_4$)alkyl, ($C_1$–$C_4$)alkoxy, ($C_1$–$C_4$)alkylamino, di-[($C_1$–$C_4$)alkyl]amino, and (C2–$C_4$)alkanoylamino; with the proviso that when Y, in the direction shown by the arrow in formula I, is —$NR^4$—$CR^3$=$CR^3$—, $R^3$ =$CH_3$ and $R^4$=H, then $R^5$ is not 4-$CH_3$, 3,5-($CH_3$)$_2$, 2,6-($CH_3$)$_2$, 2-$C_2H_5$, 4$C_2H_5$, 4n-$C_4H_9$, 2-Cl, 4-Cl, 3,4-$Cl_2$, 2-F, or 3-$CF_3$.

According to another aspect of the invention there is provided a compound as described above wherein Y, in the direction shown by the arrow in formula I is selected from —N=CR$^3$—NR$^4$—, —CR$^3$=CR$^3$—NR$^4$—, —NR—CR$^3$=CR$^3$—, —N=N—NR$^4$—, —NR$^4$—N=N—NR$^4$—, NR$^4$—N=CR$^3$, =CR$^3$—NR$^4$—CR$^3$=, —N=CR$^3$—CR$^3$=CR$^3$—, —CR$^3$=N—CR$^3$=CR$^3$—, —CR$^3$=CR$^3$—N=CR$^3$—, —CR$^3$=CR$^3$—CR$^3$=N—.

Another aspect of the invention provides a compound as described above wherein each R$^3$ is independently selected from hydrogen, hydroxy, ($C_1$–$C_4$)alkoxy, hydroxy($C_2$–$C_4$)alkoxy, amino($C_2$–$C_4$)alkyl, amino($C_2$–$C_4$)alkoxy, ($C_1$–$C_4$)alkoxy($C_2$–$C_4$)alkoxy, hydroxy($C_1$–$C_4$)alkyl($C_1$–$C_4$)alkylenedioxy, ($C_1$–$C_4$)alkoxy($C_1$–$C_4$)alkyl($C_1$–$C_4$) alkylenedioxy, mono-N- or di-N,N-($C_1$–$C_4$)alkylamino ($C_2$–$C_4$)alkoxy, 3- or 4-($C_1$–$C_4$)alkoxy-(2-hydroxy)-($C_3$–$C_4$)alkoxy, carboxy($C_1$–$C_4$)alkoxy, morpholino($C_2$–$C_4$) alkoxy, imidazol-1-yl($C_2$–$C_4$)alkoxy, 4($C_1$–$C_4$) alkylpiperazin-1-yl-($C_2$–$C_4$)alkoxy, ($C_1$–$C_4$)alkoxy($C_1$–$C_4$) alkanoyloxy, nitro, hydroxylamino, amino, phenyl, pyridyl, pyrrolo, imidazolo, thiazolo, benzimidazolo, pyridonyl, mono-N- or di-N,N-($C_1$–$C_4$)alkylamino, ($C_1$–$C_4$) alkanoylamino, hydroxy($C_2$–$C_4$)alkylamino, ($C_1$–$C_4$)alkoxy ($C_2$–$C_4$)alkylamino, ($C_1$–$C_4$)alkylsulfonamido, morpholino, ($C_1$–$C_4$)alkyl-piperazin-1-yl, bis($C_{1-4}$)alkanesulfonamido, di-N,N-($C_1$–$C_4$)alkylamino($C_2$–$C_4$)alkylamino, ($C_1$–C4) alkylamino($C_2$–$C_4$)alkylamino, piperidin-1-yl, imidazol-1-yl, pyrrolidin-1-yl, ($C_1$–$C_4$)alkoxy($C_1$–$C_4$) alkylcarbonylamino, carboxy, ($C_1$–$C_4$)alkoxycarbonyl, ($C_1$–$C_4$)alkoxycarbonyl($C_1$–$C_4$)alkoxy, amido, mono-N- or di-N,N-($C_1$–$C_4$)alkylaminocarbonyl, mono-N- or di-N,N-(hydroxy($C_2$–$C_4$)alkyl)aminocarbonyl, ($C_1$–$C_4$)alkyl$_1$, hydroxy($C_1$–$C_4$)alkyl, mono-N- or di-N,N-(($C_1$–$C_4$)alkoxy ($C_1$–$C_4$)alkyl)amino($C_1$–$C_4$)alkyl, mono-N- or di-N,N-($C_1$–$C_4$)alkylamino($C_1$–$C_4$)alkyl, ($C_1$–$C_4$)alkanoylamino ($C_1$–$C_4$)alkyl, ($C_1$–$C_4$)alkoxy($C_2$–$C_4$)alkoxy($C_1$–$C_4$)alkyl, ($C_1$–$C_4$)alkylthio, ($C_1$–$C_4$)alkoxy($C_2$–$C_4$)alkylthio or hydroxy($C_2$–$C_4$)alkylthio; and R$^4$ is selected from hydrogen, benzyl, phenyl, a ($C_2$–$C_4$)alkyl, hydroxy($C_2$–$C_4$)alkyl, or hydroxy($C_2$–$C_4$)alkyl, amino($C_2$–$C_6$)alkyl, ($C_2$–$C_4$) alkoxycarbonyl each such group substituted with amino, halo, hydroxy, ($C_2$–$C_4$)alkanoyloxy, ($C_1$–$C_4$)alkoxy, mono-N- or di-N,N-($C_1$–$C_4$)alkylamino, mono-N or di-N,N-(hydroxy($C_2$–$C_4$)alkyl)amino, mono-N or di-N,N-(($C_1$–$C_4$) alkoxy($C_2$–$C_4$)alkyl)amino, sulfonylaryl($C_1$–$C_4$) alkylamine, ($C_1$–$C_4$)alkanoylamino, imidazol-1-yl, piperidino, morpholino, piperazin-1-yl-, 4($C_1$–$C_4$) alkylpiperazin-1-yl-, pyridyl, pyrrolo, imidazolo, thiazolo, pyridenyl, carboxy, ($C_1$–$C_4$)alkoxycarbonyl, carbamoyl, mono-N- or di-N,N-($C_1$–$C_4$)alkylcarbamoyl, carboxamido, mono-N- or di-N,N-($C_1$–$C_4$)alkylcarboxamido or mono-N- or di-N,N-(hydroxy($C_2$–$C_4$)alkyl)carboxamido.

Yet another aspect of the invention provides a compound as described above wherein Y in the direction shown by the arrow in formula I is selected from —CR$^3$=CR$^3$—NR$^4$—, —NR$^4$—CR$^3$=CR$^3$— and —CH=CR$^3$—N=CH—.

According to another aspect of the invention there is provided a compound as described above wherein Y, in the direction shown by the arrow in formula I is selected from —NR$^4$—CR$^3$=CR$^3$—, or —CH=CR$^3$—N=CH— and —CR$^3$=CR$^3$—NR$^4$—.

Yet another aspect of the invention provides a compound as described above wherein Y, in the direction shown by the arrow in formula 1, is —CR$^3$=CR$^3$—NR$^4$—and R$^4$ is hydrogen.

Another aspect of the invention provides a compound as described above wherein R$^1$R$^2$N is

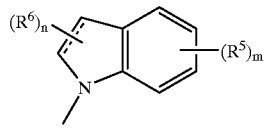

and R$^5$, R$^6$, m and n are as defined above.

According to another aspect of the invention there is provided a compound as described above wherein each R$^5$ is Independently selected from 4-hydroxy, 4amino, fluoro, 5-hydroxy, 5-amino, 6-halo, 6methyl, 6-ethenyl, 6-ethynyl, 6-nitro and 7-methyl and each R$^6$ is independently selected from hydroxy, amino, N-mono- or N,N-di-($C_1$–$C_4$) alkylamino, sulfo, or ($C_1$–$C_4$)alkoxy (provided that such groups are not attached to a ring carbon which is directly adjacent to the ring N-), or R$^6$ for each occurrence is independently carboxy, hydroxy($C_1$–$C_4$)alkyl, ($C_1$–$C_4$) alkoxy($C_1$–$C_4$)alkyl, amino($C_1$–$C_4$)alkyl, mono-N- or di-N, N-($C_1$–$C_4$)alkylamino($C_1$–$C_4$)alkyl, morpholino ($C_1$–$C_4$) alkyl, 4-($C_1$–$C_4$)alkyl-piperazin-1-yl($C_1$–$C_4$)alkyl, carboxy ($C_1$–$C_4$)alkyl, ($C_1$–$C_4$)alkoxycarbonyl, sulfo($C_1$–$C_4$)alkyl, pyridyl($C_1$–$C_4$)alkyl and ($C_1$–C4)alkyl.

Another aspect of the invention provides a compound as described above wherein R$^1$ is H and R$^2$ is (R$^5$)$_m$-substituted phenyl wherein R$^5$ and m are as defined above.

Yet another aspect of the invention provides a compound as described above wherein each R$^5$ is independently selected from 4fluoro-3-chloro, 3-trifluoromethyl, 4-fluoro-3-trifluoromethyl, 3-nitro-4-chloro, 3-nitro-4-fluoro, 4-fluoro-3-bromo, 3-iodo-5-amino, 3-methyl-4-fluoro, 4-amino, 3-fluoro, 3-hydroxy, 3-amino, 3-halo, 3-methyl, 3-ethenyl, 3-ethynyl, 3-nitro and 4-methyl.

According to another aspect of the invention there is provided a compound as described above wherein R$^1$ is H and R$^2$ is Q.

Another aspect of the invention provides a compound as described above wherein Q is selected from pyrrolo 1,2,3, 5-tetrahydro-pyrrolo[2,3-f]indole, 4-, 5-, 6-indolyl, 1H-benzimidazol4yl, 1H-benzimidazol-5-yl, 1H-indazol-4-yl, 1H-indazol-5-yl, 1H-indazol-6-yl, 1H-indazol-7-yl, 1H-benzotrizol-4-yl, 1H-benzotrizol-5-yl, 1H-benzotrizol-6-yl, 5- or 6-benzoxazolyl, 5- or 6-benzothiazolyl, benzo[c] [2,1,3]thiadiazol-4-yl, 2-, 3-, 4-, 5-, 6-, 7- or 8-quinolyl, 1-, 3-, 4-, 5-, 6-, 7- or 8-isoquinolyl, 4-, 5-, 6-, 7- or 8cinnolinyl, 5-, 6-, 7- or 8-quinazolinyl, or 2-, 5-, or 6-quinoxalinyl, which may optionally bear one or two substituents selected from fluoro, bromo, chloro, methyl, ethyl, ethenyl, ethynyl and methoxy.

Yet another aspect of the invention provides a compound as described above wherein Q is selected from pyrrolo 5-indolyl, 1H-indazol-5-yl, 1H-benzotriazol-5-yl, 6-benzothiazolyl, benzo[c][2,1,3]thiadiazol-4-yl, 5quinolyl, 6quinolyl, 8quinolyl, 5-isoquinolyl, or 5quinocalinyl, which may optionally bear one or two substituents selected from fluoro, bromo, chloro, methyl, ethyl, ethenyl, ethynyl and methoxy.

Preferred compounds of formula I are selected from the group consisting of
(3-ethynyl-phenyl)-(7H-pyrrolo[2,3-d]pyrimidin-4-yl)-amine hydrochloride;
(3-chloro-phenyl)-(7H-pyrrolo[2,3-d]pyrimidin-4-yl)-amine hydrochloride;
4-(6-chloro-2,3-dihydro-indol-1-yl)7H-pyrrolo[2,3-d] pyrimidine hydrochloride;

(7H-pyrrolo[2,3-d]pyrimidin-4-yl)m-tolyl-amine hydrochloride;
(1H-indol-5-yl)-(7H-pyrrolo [2,3-d]pyrimidin-4-yl)-amine hydrochloride;
(6-methylindolin-1-yl)-(7H-pyrrolo[2,3-d]pyrimidin-4-yl)-amine;
(benzo[b]thien-5-yl)-(7H-pyrrolo[2,3-d]pyrimidin-4-yl)-amine;
(6-chloro-5-fluoroindolin-1-yl)-(7H-pyrrolo[2,3-d]pyrimidin-4-yl)-amine;
(1H-indazol-5-yl)-(7H-pyrrolo[2,3]pyrimidin-4-yl)-amine;
1-(4-m-tolylamino-pyrrolo[2,3-d]pyrimidin-7-yl)-ethanone hydrochloride;
(5-iodo-7H-pyrrolo[2,3-d]pyrimidin-4-yl)-m-tolyl-amine;
(3-chloro-phenyl)-(1H-[1,2,3]triazolo[4,5-d]pyrimidin-7-yl)-amine hydrochloride:
(3-chloro-phenyl-pyrido[4,3-d]pyrimidin-4-yl-amine hydrochloride;
(1H-indol-5-yl)-pyrido[4,3-d]pyrimidin-4-yl-amine hydrochloride;
(3-ethynylphenyl)-(7-methyl-pyrido[4,3-d]pyrimidin-4-yl)-amine hydrochloride;
(3-chloro-phenyl)-(7-methyl-pyrido[4,3-d]pyrimidin-4-yl)-amine hydrochloride;
(3-ethynyl-phenyl)-(pyrido[4,3-d]pyrimidin-4-yl)-amine hydrochloride;
(6-bromo-5-fluoroindolin-1-yl)-(pyrido[4,3-d]pyrimidin-4-yl)-amine;
(6-chloro-5-fluoroindolin-1-yl)-(pyrido[4,3-d]pyrimidin-4-yl)-amine;
(1H-indazol-5-yl)-(pyrido[4,3-d]pyrimidin-4-yl)-amine;
(3-methyl-4-hydroxyphenyl)(6methylpyrido[4,3-d]pyrimidin-4-yl)-amine;
(6-iodoindolin-1-yl)-(pyrido[4,3-d]pyrimidin-4-yl)-amine;
(benzo[b]thien-5-yl)-(pyrido[4,3-d]pyrimidin-4-yl)-amine;
(3-ethynyl-phenyl)-(9H-purin-6-yl)-amine;
(1H-indol-5-yl)-(9H-purin-6-yl)-amine hydrochloride;
(3-chloro-phenyl)-(9H-purin-6-yl)-amine hydrochloride;
4-(6-chloro-2,3-dihydro-indol-1-yl)-pyrido[3,4-d]pyrimidine;
(pyrido[3,4-d]pyrimidin-4-yl)-(m-tolyl)-amine;
(1H-indazol-5-yl)-(pyrido[3,4-d]pyrimidin-4-yl)-amine;
(1H-indol-5-yl)-(pyrido[3,4-d]pyrimidin-4-yl)-amine;
(phenyl)-(pyrido[2,3-d]pyrimidin-4-yl)-amine;
(3-chloro-phenyl)-(pyrido[2,3-d]pyrimidin-4-yl)-amine;
(3-chloro-phenyl)-(pyrido[3,4-d]pyrimidin-4-yl)-amine;
(3-bromo-phenyl)-(pyrido[3,4-d]pyrimidin-4-yl)-amine;
(phenyl)-(pyrido[3,4-d]pyrimidin-4-yl)-amine;
4-(6-chloro-2,3dihydro-indol-1-yl)-pyrido[3,4-d]pyrimidine;
(pyrido[3,4-d]pyrimidin-4-yl)-(m-tolyl)-amine;
(1H4-indazol-5-yl)-pyrido[3,4-d]pyrimidin-4-yl-amine;
(1H-indol-5-yl)-pyrido[3,4-d]pyrimidin-4-yl-amine;
phenyl-pyrido[2,3-d]pyrimidin-4-yl-amine;
(3-chloro-phenyl-pyrido[2,3-d]pyrimidin-4-yl-amine;
(3-chloro-phenyl-pyrido[3,4-d]pyrimidin-4-yl-amine;
(3-bromo-phenyl-pyrido[3,4-d]pyrimidin-4-yl-amine;
phenyl-pyrido[3,4-d]pyrimidin-4-yl-amine;
(7-benzenesulfonyl-7H-pyrrolo[2,3-d]pyrimidin-4-yl)-(3ethynyl-phenyl)-amine;
4-(6-chloro-2,3-dihydro-indol-1-yl)-5H-pyrrolo[3,2-d]pyrimidin-6-ol;
(3-ethynyl-phenyl)-[7-(2-morpholin-4-yl-ethyl)-7H-pyrrolo[2,3-d]pyrimidin-4-yl]-amine;
(3-ethynyl-phenyl)-[7-(2-methoxy-ethyl)-7H-pyrrolo[2,3-d]pyrimidin-4-yl]-amine;
(3-ethynyl-phenyl)-{7-[2-(2-mothoxy-ethoxy)-ethyl]-7H-pyrrolo[2,3-d]pyrimidin-4-yl}-amine;
(7-allyl-pyrrolo[2,3-d]pyrimidin-4-yl)-(3-ethynyl-phenyl)-amine hydrochloride;
(3-ethynyl-phenyl)-(7-methyl-pyrrolo[2,3-d]pyrimidin-4yl)-amine hydrochloride;
(5-bromo-7H-pyrrolo[2,3-d]pyrimidin-4-yl)-(3-ethynyl-phenyl)-amine;
(3-ethynyl-phenyl)-(6-iodo-7H-pyrrolo[2,3-d]pyrimidin-4-yl)-amine;
4-(3-ethynyl-phenylamino)-7H-pyrrolo[2,3-d]pyrimidine-5-carboxylic acid;
(3-ethynyl-phenyl)-(5-methyl-7H-pyrrolo[2,3-d]pyrimidin-4-yl)-amine hydrochloride;
N-(5-iodo-7H-pyrrolo[2,3-d]pyrimidin-4-yl)-N-m-tolyl-acetamide;
4-(3-ethynyl-phenylamino)-7H-pyrrolo[2,3-d]pyrimidin-5-carboxylic acid methyl esterhydrochloride;(3-ethynyl-phenyl)-(5-cyano-7H-pyrrolo[2,3-d]pyrimidin-4-yl)-amine;
(1H-indazol-5-yl)-(6-methyl-pyrido[3,4-d]pyrimidin-4-yl)-amine hydrochloride; benzo[b]thiophen-5-yl-(6-methyl-pyrido[3,4-d]pyrimidin-4-yl)-amine hydrochloride;
(3-ethynyl-4-fluoro-phenyl)-(6-methyl-pyrido[3,4-d]pyrimidin-4-yl)-amine;
2-methyl-4-(6-methyl-pyrido[3,4-d]pyrimidin-4-ylamino)-phenol dihydrochloride;
4-(4-bromo-7-methyl-2,3-dihydro-indol-1-yl)-6-methyl-pyrido[3,4-d]pyrimidine hydrochloride;
4-(6-bromo-7-methyl-2,3-dihydro-indol-1-yl)-6-methyl-pyrido[3,4-d]pyrimidine hydrochloride;
4-(6-bromo-6-fluoro-2,3-dihydro-indol-1-yl)-6-methyl-pyrido[3,4-d]pyrimidine hydrochloride;
(3-chloro-4-fluoro-phenyl)-(6-methyl-pyrido[3,4-d]pyrimidin-4-yl)-amine hydrochloride;
(6-methyl-pyrido[3,4-d]pyrimidin-4-yl)-(3-trifluoromethyl-phenyl)-amine hydrochloride;
(4-fluoro-3-methyl-phenyl)-(6-methyl-pyrido[3,4-d]pyrimidin-4-yl)-amine hydrochloride;
2-iodo-4-(6-methyl-pyrido[3,4-d]pyrimidin-4-ylamino)-phenol hydrochloride;
(4-bromo-3-fluoro-phenyl)-(6-methyl-pyrido[3,4-d]pyrimidin-4-yl)-amine hydrochloride;
4-(6,7-dimethyl-2,3-dihydro-indol-1-yl)-pyrido[3,4-d]pyrimidine hydrochloride;
(3ethynyl-phenyl)-pyrido[3,4-d]pyrimidin-4-yl-amine hydrochloride;
benzo[b]thiophen-5-yl-pyrido[3,4-d]pyrimidin-4-yl-amine hydrochloride;
(3-ethynyl-phenyl)-(6-methyl-pyrido[3,4-d]pyrimidin-4-yl)-amine hydrochloride; 4-(6-chloro-2,3-dihydro-indol-1-yl)-6-methyl-pyrido[3,4-d]pyrimidine;
(3-ethynyl-phenyl)-(5-methylsulfanyl-7H-pyrrolo[2,3]pyrimidin-4-yl)-amine; and
(1H-indol-5-yl)-(6-methyl-pyrido[3,4-d]pyrimidin-4-yl)-amine methanesulfonate.

Most preferred compounds of the formula I as described above are selected from
(1H-indol-5-yl)-(methyl-pyrido[3,4-d]pyrimidin-4-yl)-amine;
(3-ethynyl-phenyl)-(6-methyl-pyrido[3,4-d]pyrimidin-4-yl)-amine;
(3-ethynyl-phenyl)-(7H-pyrrolo[2,3-d]pyrimidin-4-yl)-amine;
(3-chloro-phenyl)-(7H-pyrrolo[2,3-d]pyrimidin-4-yl)-amine;
(3-ethynyl-phenyl)-(5-methyl-7H-pyrrolo[2,3-d]pyrimidin-4-yl)-amino;
4-(3-ethynyl-phenylamino)-7H-pyrrolo[2,3-d]pyrimidine-5-carboxylic acid methyl ester;

4-(3-ethynyl-phenylamino)-7H-pyrrolo[2,3-d]pyrimidine-5-carbonitrile;
(1H-indol-5-yl)-pyrido[3,4-d]pyrimidin-4-yl-amine;
(3chloro-4-fluoro-phenyl)-(6-methyl-pyrido[3,4-d]pyrimidin-4-yl)-amine;
benzo[b]thiophen-5-yl-(6-methyl-pyrido[3,4-d]pyrimidin-4-yl)-amine;
(3-ethynyl-phenyl)-pyrido[3,4-d]pyrimidin-4-yl-amine;
(4-fluoro-3-methyl-phenyl)-(6methyl-pyrido[3,4-d]pyrimidin-4-yl)-amine;
4-(6chloro-2,3-dihydro-indol-1-yl)-pyrido[3,4-d]pyrimidine;
pyrido[3,4-d]pyrimidin-4-yl-m-tolyl-amine;
(6-methyl-pyrido[3,4-d]pyrimidin-4-yl)-(3-trifluoromethyl-phenyl)-amine;
(1H-indazol-5-yl)-(6methyl-pyrido[3,4-d]pyrimidin-4-yl)-amine;
(3-ethynyl-phenyl)-(5-methylsulfonyl-7H-pyrrolo[2,3-d]pyrimidin-4-yl)-amine;
(1H-indol-5-yl)-(7H-pyrrolo[2,3-d]pyrimidin 4-yl)-amine;
(5-bromo-7H-pyrrolo[2,3-d]pyrimidin-4-yl)-(3-ethynyl-phenyl)-amine;

The invention also provides a compound of the formula

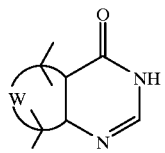

II wherein W, in the direction indicated by the arrows, is selected from —CH$_2$=C(CH$_3$)—N=CH$_2$—, —CH$_2$=N—C(CH$_3$)=CH$_2$— and =C(CH$_3$)—NH—CH=.

According to another aspect of the invention there is provided a compound as described above wherein W is —CH$_2$=C(CH$_3$)—N=CH$_2$—.

Another aspect of the invention provides a compound as described above wherein W is —CH$_2$=N—C(CH$_3$)=CH$_2$—.

Yet another aspect of the invention provides a compound as described above wherein W is =C(CH$_3$)—NH—CH=.

The invention also provides a method of treating hyperproliferative disorders which comprises administering to a mammal in need of such treatment a hyperproliferative disorder treating amount of a compound of formula I.

According to another aspect of the invention there is provided a method as described above wherein the hyperproliferative disease is cancer.

Yet another aspect of the invention provides a method as described above wherein the disease is brain, lung, squamous cell, bladder, gastric, pancreatic, hepatic, renal, colorectal, breast, head, neck, oesophageal, gynecological or thyroid cancer.

Another aspect of the Invention provides a method as described above wherein the hyperproliferative disorder is noncancerous.

Another aspect of the invention provides a compound as described above wherein the noncancerous hyperproliferative disorder is psoriasis or benign prostatic hyperplasia.

The invention further provides a pharmaceutical composition for the treatment of hyperproliferative disorder in a mammal which comprises a hyperproliferative disease treating amount of a compound of formula I and a pharmaceutically acceptable carrier.

In the present application certain terms are defined as follows:

By halo is meant chloro, bromo, iodo, or fluoro.

By alkyl is meant straight chain or, when C$_3$ or larger, a cyclic or, when C$_2$ or larger, a branched saturated hydrocarbon.

As used herein, the expression "reaction-inert solvents" refers to a solvent which does not interact with starting materials, reagents, intermediates or products in a manner which adversely affects the yield of the desired product.

Other features and advantages will be apparent from the specification and claims which describe the invention.

DETAILED DESCRIPTION OF THE INVENTION

The Formula I compounds, or pharmaceutically acceptable salts and prodrugs thereof can be prepared by any process known to be applicable to the preparation of chemically-related compounds.

SCHEME

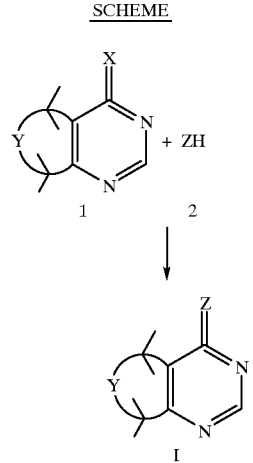

As shown in the Scheme the Formula I compounds can, generally, be made prepared from the 4-chloro or hydroxy derivatives of the appropriately substituted heteroaryl-fused pyrimidine 1 using the appropriately substituted amine ZH 2.

Typically the appropriately substituted 4-haloheteroaryl-fused pyrimidine 1 (or a heteroaryl-fused pyrimidine bearing a suitable displaceable leaving group in the 4-position such as aryloxy, alkyl sulfinyloxy such as trifluoromethanesulfonyloxy, arylsulfinyloxy, siloxy, cyano, pyrazolo, triazolo ortetrazolo), preferably a haloheteroaryl such as 4-chloroheteroaryl derivative, is reacted with the appropriate amine 2 in a solvent such as a (C$_1$–C$_6$)alcohol, dimethylformamide (DMF), N-methylpyrrolidin-2-one, chloroform, acetonitrile, tetrahydrofuran (THF), dimethylsulfoxide (DMSO), 1-4 dioxane, pyridine or other aprotic solvent. The combination can be effected in the presence of a base, preferably an alkali or alkaline earth metal carbonate or hydroxide or a tertiary amine base, such as pyridine, 2,6-lutidine, collidine, N-methyl-morpholine, triethylamine, diethyl isopropyl amine, 4-dimethylamino-pyridine or N,N-dimethylaniline. These bases are hereinafter referred to as "suitable bases". The mixture is maintained at a temperature of from ambient to reflux, preferably from about 35° C. to reflux, until substantially no remaining 4-haloheteroaryl-fused pyrimidine can be detected, typically about 2 hours to about 72 hours. The reaction is preferably performed under an inert atmosphere such as dry nitrogen gas.

Generally, the reactants are combined stoichiometrically when a suitable amine base is used, although, for those compounds where a salt (typically the HCl salt) of the amine is used, it is preferable to use excess amine 2, generally an extra equivalent of the amine 2. Alternatively, if an amine base is not used an excess of the amine reactant may be used)

For those compounds where a sterically hindered amine (such as a 2-alkylindoline) or very reactive 4-haloheteroaryl-fused pyrimidine is used it is preferable to use t-butyl alcohol or a polar aprotic solvent such as dimethylformamide or N-methylpyrrolidin-2-one as the solvent.

Other Formula I compounds may be prepared by the following appropriate reactions subsequent to the above coupling.

Compounds of Formula I wherein $R^3$ or $R^5$ is a primary amino or hydroxyamino may be prepared by the reduction of Formula I compounds wherein $R^3$ or $R^5$ is a nitro group.

The reduction may conveniently be carried out by any of the many procedures known for such transformations, The reduction may be carried out, for example, by the hydrogenation of a solution of the nitro compound in a reaction-inert solvent in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a solvent such as a mixture of water and an alcohol, for example, methanol or ethanol, to a temperature in the range, for example, 50 to 150° C., conveniently at or near 70° C.

For the production of those compounds of Formula I wherein $R^5$ or $R^6$ incorporates a primary or secondary amino moiety (other than the amino group intended to react with the quinazoline), such free amine is preferably protected prior to the above described reaction followed by deprotection, subsequent to the above described reaction with 4-haloquinazoline.

For a description of protecting groups and their use, see T. W. Greene and P. G. M. Wuts, "Protective Groups in Organic Synthesis" Second Ed., John Wiley & Sons, New York, 1991.

Nitrogen protecting groups are well known in the art, including ($C_1$–$C_6$)alkoxycarbonyl, optionally substituted benzyloxycarbonyl, aryloxycarbonyl, tributyl, vinyloxycarbonyl, O-nitrophenylsulfonyl, diphenylphosphinyl, p-toluenesulfonyl, and benzyl. The addition of the nitrogen protecting group may be carried out in a chlorinated hydrocarbon solvent such as methylene chloride or 1,2-dichloroethane, or an ethereal solvent such as glyme, diglyme or THF, in the presence or absence of a tertiary amine base such as triethylamine, diisopropylethylamine or pyridine, preferably triethylamine, at a temperature from about 0° C. to about 50° C., preferably about ambient temperature. Alternatively, the protecting groups are conveniently attached using Schotten-Baumann conditions.

Subsequent to the above described amine coupling reaction the protecting group may be removed by deprotecting methods known to those skilled in the art such as trifluoroacetic acid in methylene chloride for the tert-butoxycarbonyl protected products.

Compounds of the Formula I wherein $R^3$ is hydroxy, may preferably be prepared by cleavage of a Formula I compound wherein $R^3$ is ($C_1$–$C_4$)alkoxy.

The cleavage reaction may conveniently be carried out by any of the many procedures known for such a transformation. Treatment of the heteroaryl-fused pyrimidine derivative of Formula I with molten pyridine hydrochloride (20–30 eq.) at 150 to 175° C. may be employed for O-dealkylations. Alternatively, the reaction may be carried out, for example, by treatment of the heteroaryl-fused pyrimidine derivative with an alkali metal ($C_1$–$C_4$)alkylsulphide such as sodium ethanethiolate or, for example, by treatment with an alkali metal diarylphosphide such as lithium diphenylphosphide. Alternatively the cleavage reaction may conveniently be carried out, for example, by treatment of the heteroaryl-fused pyrimidine derivative with a boron or aluminum trihalide such as boron tribromide. Such reactions are preferably carried out in the presence of a reaction-inert solvent and at a suitable temperature.

For the production of those compounds of Formula I wherein $R^3$ is a ($C_1$–$C_4$)alkylsulphonyl or ($C_1$–$C_4$) alkylsulphonyl group, the oxidation of a Formula I compound wherein $R^3$ is a ($C_1$–$C_4$)alkylthio group Is preferred.

A suitable oxidizing agent is, for example, an agent known in the art for the oxidation of thio to sulphinyl and/or sulphenyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidizing agent in order to reduce the risk of over oxidation and damage to other functional groups. In general the reaction is carried out in a suitable solvent such as methylene chloride, chloroform, acetone, tetrahydrofuran or ter-butyl methyl ether and at a temperature, for example, –25 to 50° C., conveniently at or near ambient temperature, that is in the range of 15 to 35° C. When a compound carrying a sulphinyl group is required a milder oxidizing agent may also be used, for example sodium or potassium metaperiodate, conveniently in a polar solvent such as acetic acid or ethanol. It will be appreciated that when a compound of the Formula I containing a ($C_1$–$C_4$)alkylsulphonyl group is required, it may be obtained by oxidation of the corresponding ($C_1$–$C_4$)alkylsulphonyl compound as well as of the corresponding ($C_1$–$C_4$)alkylthio compound.

For the production of those compounds of Formula I wherein $R^3$ is ($C_2$–$C_4$)alkanoylamino or substituted ($C_2$–$C_4$) alkanoylamino, ureido, 3-phenylureido, benzamido, or sulfonamido, the acylation or sulfonylation of a Formula I compound wherein $R^3$ is amino is appropriate.

A suitable acylating agent is, for example, any agent known in the art for the acylation of amino to acylamino, for example an acyl halide (e.g., a ($C_2$–$C_4$)alkanoyl chloride or bromide or a benzoyl chloride or bromide), an alkanoic acid anhydride or mixed anhydride (e.g., ($C_2$–$C_4$)alkanoic acid anhydride such as acetic anhydride or the mixed anhydride formed by the reaction of an alkanoic acid and a ($C_1$–$C_4$) alkoxycarbonyl halide, for example ($C_1$–$C_4$)alkoxycarbonyl chloride, in the presence of a suitable base). For the production of those compounds of Formula I wherein $R^1$ is ureido or 3-phenylureido, a suitable acylating agent is, for example, a cyanate, for example an alkali metal cyanate such as sodium cyanate or, for example, an isocyanate such as phenyl isocyanate. N-sulfonylations may be carried out with suitable sulfonyl halides or sulfonylanhydrides in the presence of a tertiary amine base. In general the acylation or sulfonylation is carried out in a reaction-inert solvent and at a temperature, in the range, for example, –30 to 120° C., conveniently at or near ambient temperature.

For the production of those compounds of Formula I wherein $R^3$ is ($C_1$–$C_4$)alkoxy or substituted ($C_1$–$C_4$)alkoxy or $R^1$ is $(C_1-C_4)$alkylamino or substituted mono-N- or di-N,N-$(C_1-C_4)$alkylamino, the alkylation, preferably in the presence of a suitable base, of a Formula I compound wherein $R^1$ is hydroxy or amino, as appropriate, is preferred.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a $(C_1-C_4)$alkyl chloride, bromide or iodide or a substituted $(C_1-C_4)$alkyl chloride, bromide or iodide, in the presence of a suitable base in a reaction-inert solvent and at a temperature in the range, for example, 10 to 140° C., conveniently at or near ambient temperature.

For the production of those compounds of Formula I wherein $R^3$ is an amino-, oxy- or cyano-substituted $(C_1-C_4)$ alkyl substituent, the reaction, preferably in the presence of a suitable base, of a Formula I compound wherein $R^3$ is a $(C_1-C_4)$alkyl substituent bearing a displaceable group with an appropriate amine, alcohol or cyanide is appropriate.

The reaction is preferably carried out in a reaction-inert solvent or diluent and at a temperature in the range, for example, 10 to 100° C., conveniently at or near ambient temperature.

For the production of those compounds of Formula I wherein $R^3$, $R^5$, or $R^6$ is a carboxy substituent or a substituent which includes a carboxy group, the hydrolysis of a Formula I compound wherein $R^3$, $R^5$, $R^6$ is a $(C_1-C_4)$ alkoxycarbonyl substituent or a substituent which includes a $(C_1-C_4)$alkoxycarbonyl group is desirable.

The hydrolysis may conveniently be preformed, for example, under basic conditions such as an alkali metal hydroxide mediated hydrolysis as illustrated in the accompanying Examples.

For the production of those compounds of Formula I wherein $R^3$ is amino, $(C_1-C_4)$alkylamino,di-[$(C_1-C_4)$alkyl] amino,pyrrolidin-1-yl, piperidino,morpholino,piperazin-1-yl, 4-$(C_1-C_4)$alkylpiperazin-1-yl or $(C_1-C_4)$alkythio, the reaction, conveniently in the presence of a suitable base, of a Formula I compound wherein $R^3$ is a displaceable group with an appropriate amine or thiol is preferred.

The reaction is preferably carried out in a reaction-inert solvent or diluent and at a temperature in the range, for example, 10 to 180° C., conveniently in the range 100 to 150° C.

For the production of those compounds of Formula I wherein $R^3$ is 2-oxopyrrolidin-1-yl or 2-oxopiperidin-1-yl, the cyclisation, in the presence of a suitable base, of a Formula I compound wherein $R^3$ is a halo-$(C_2-C_4)$ alkanoylamino group is convenient.

The reaction is preferably carried out in a reaction-inert solvent or diluent and at a temperature in the range, for example, 10 to 100° C., conveniently at or near ambient temperature.

For the production of compounds of Formula I in which $R^3$ is carbamoyl, substituted carbamoyl, alkanoyloxy or substituted alkanoyloxy, the carbamoylation or acylation of a Formula I compound wherein $R^3$ is hydroxy is convenient.

Suitable acylating agents are for example any agent known in the art for acylation of hydroxyaryl moieties to alkanoyloxy aryl. For example, $(C_2-C_4)$alkanoyl halides, $(C_2-C_4)$alkanoyl anhydrides or mixed anhydrides, and suitable substituted derivatives thereof may be employed typically In the presence of a suitable base. Alternatively, $(C_2-C_4)$alkanoic acids or suitably substituted derivatives thereof may be coupled with a Formula I compound wherein $R^3$ is hydroxy with the aid of a condensing agent such as a carbodiimide. For the production of those compounds of Formula I in which $R^3$ is carbamoyl or substituted carbamoyl, suitable carbamoylating agents are for example a cyanate or an alkyl or arylisocyanate, typically in the presence of a suitable base. Alternatively a suitable intermediate such as the chloroformates or imidazolylacarbonyl derivative of a heteroaryl-fused pyrimidine of Formula I in which $R^3$ is hydroxy may be generated, for example by treatment of said derivative with phosgene (or a phosgene equivalent) or carbonyldiimidazole. The resulting intermediate may then be reacted with an appropriate amine or substituted amine to produce the desired carbamoyl derivatives.

For the production of heteroaryl-fused pyrimidine derivatives of Formula I wherein $R^3$ is aminocarbonyl or a substituted aminocarbonyl, the aminolysis of a suitable intermediate derived from a heteroaryl-fused pyrimidine of Formula I in which $R^3$ is carboxy is preferred.

The activation and coupling of a Formula I compound wherein $R^3$ is carboxy may be performed by a variety of methods known to those skilled in the art. Suitable methods include activation of the carboxyl as an acid halide, azide, symmetric or mixed anhydride, or active ester of appropriate reactivity for coupling with the desired amine. Examples of such types of intermediates and their production and use in couplings with amines may be found extensively in the literature; for example M. Bodansky and A. Bodansky, "The Practice of Peptide Synthesis", Springer,-Verlag, New York, 1984.

The resulting Formula I compounds may be isolated and purified by standard methods, such as solvent removal and recrystallization or chromatography, if desired.

Optionally substituted indole and indolines, useful in the practice of the invention, and methods for their preparation, are described in co-pending U.S. application Ser. No. 08/200,359, incorporated herein by reference. In addition to methods described therein the preparation of various indolines, indoles, oxindoles, and isatins useful as intermediates are further described in "Heterocyclic Compounds with Indole and Carbazole Systems", W. C. Sumpter and F. M. Miller, in Vol. 8 of "The Chemistry of Heterocyclic Compounds" Series, Interscience Publishers Inc., N.Y., 1954 and references contained therein.

Substituted anilines, useful in the practice of the invention, and methods for their preparation, are described in co-pending U.S. application Ser. No. 08/413,300 and PCT application no. PCT/IB95/00436, incorporated herein by reference.

Compounds of the formula ZH wherein ZH is $QNH_2$, useful in the practice of the invention, and methods for their preparation, are described in European Patent application serial no. EP 0 496 617 A1 incorporated herein by reference.

Certain compounds of Formula I can exist in solvated as well as unsolvated forms such as, for example, hydrated forms. It is to be understood that the invention encompasses all such solvated as well as unsolvated forms which possess activity against hyperproliferative diseases.

A suitable pharmaceutically-acceptable salt of a heteroaryl-fused pyrimidine derivative of the invention is, for example, an acid-addition salt of a heteroaryl-fused pyrimidine derivative of the invention which is sufficiently basic, for example an acid-addition salt with, for example, an inorganic or organic acid, for example, hydrochloric, hydrobromic, sulphuric, phosphoric, methanesulfonic, benzenesulfonic, trifluoroacetic, citric, lactic or maleic acid. In addition a suitable pharmaceutically-acceptable base-addition salt of a heteroaryl-fused pyrimidine derivative of the invention which is sufficiently acidic is an alkali metal salt, for example a lithium, sodium or potassium salt; an alkaline earth metal salt, for example a calcium or magnesium salt; an ammonium salt; or a salt with an organic base which affords a physiologically-acceptable cation for example a salt with methylamine, dimethylamine, trimethylamine, piperidine, morpholine or tris-(2-hydroxyethyl)amine. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent, preferably an ethereal or hydrocarbon solvent, followed by filtration, by evaporation of the solvent, or, in the case of aqueous solutions, by lyophilizaton, as appropriate.

Some of the compounds of Formula I have asymmetric carbon atoms. Such diasteromeric mixtures can be separated into their individual diastereomers on the basis of their physical chemical differences by methods known per se., for example, by chromatography and/or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomer. All such isomers, including diastereomers and enantiomers are considered as part of the invention.

The compounds of this invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer) in mammals, particularly humans. In particular, the compounds of this invention are therapeutants or prophylactics for the treatment of a variety of human tumors (renal, liver, kidney, bladder, breast, gastric, ovarian, colorectal, prostate, pancreatic, lung, vulval, thyroid, hepatic carcinomas, sarcomas, glioblastomas, various head and neck tumors), and other hyperplastic conditions such as benign hyperplasia of the skin (e.g., psoriasis) or prostate (e.g., BPH). It is in addition expected that a heteroaryl-fused pyrimidine of the present invention may possess activity against a range of leukemias and lymphoid malignancies.

The compounds of Formula I may also be expected to be useful in the treatment of additional disorders in which aberrant expression ligand/receptor interactions, activation or signalling events related to various protein tyrosine kinases, (e., IGF-receptors) whose activity is inhibited by the agents of Formula I, are involved.

Such disorders may include those of neuronal, glial, astrocytal, hypothalamic, and other glandular, macrophagal, epithelial, stromal, and blastocoelic nature in which aberrant function, expression, activation or signalling of the tyrosine kinases may be involved. In addition, compounds of Formula I may have therapeutic utility in inflammatory, angiogenic and immunologic disorders involving both identified and as yet unidentified tyrosine kinases which are inhibited by compounds of Formula I.

The in vitro activity of these compounds in inhibiting the receptor tyrosine kinase (and thus subsequent proliferative response, e.g., cancer) may be determined by a procedure as detailed below. Activity of compounds of Formula I in vitro can be determined by the amount of inhibition of the phosphorylation of an exogenous substrate (e.g., Lys$_3$—Gastrin or polyGluTyr (4:1) random copolymer (I. Posner et. al., J. Biol. Chem. 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, Methods in Enzymology 146, 82–88 (1987) from A431 cells (American Type Culture Collection, Rockville, Md.) and preincubated in a microfuge tube with EGF (2 $\mu$g/ml) in phosphorylation buffer+ vanadate (PBV: 50 mM HEPES, pH 7.4; 125 mM NaCl; 24 mM MgCl$_2$; 100 $\mu$M sodium orthovanadate), in a total volume of 10 $\mu$l, for 20–30 minutes at room temperature. The test compound, dissolved in dimethylsulfoxide (DMSO), is diluted in PBV*, and 10 $\mu$l is mixed with the EGF receptor /EGF mix, and incubated for 10–30 minutes at 30° C. The phosphorylation reaction is initiated by addition of 20 $\mu$l $^{33}$P-ATP/substrate mix (120 $\mu$M Lys$_3$-Gastrin (sequence in single letter code for amino acids, KKKGPWLEEEEEAYGWLDF), 50 mM Hepes pH 7.4, 40 $\mu$M ATP, 2 $\mu$Ci $\gamma$-[$^{33}$P]-ATP) to the EGFr/EGF mix and incubated for 20 minutes at room temperature. The reaction is stopped by addition of 10 $\mu$l stop solution (0.5 M EDTA, pH 8; 2 mM ATP) and 6 $\mu$l 2N HCl. The tubes are centrifuged at 14,000 RPM, 4° C., for 10 minutes. 35 $\mu$l of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., lys$_3$-gastrin) is subtracted from all values as a background and percent inhibition is calculated relative to controls without test compound present.

Such assays carried out with a range of doses of test compounds allow the determination of an approximate IC$_{50}$ value for the in vitro inhibition of EGFR kinase activity. Although the inhibitory properties of the compounds of Formula I vary with structural change as expected, in general, the activity exhibited by these agents determined in the manner described above is in the range of IC$_{50}$=0.0001–30 $\mu$M.

Activity of compounds of Formula I in vivo can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep.* (Part 2)", 5, 169–186 (1975), with slight modifications. Tumors are induced in the left flank by s.c. injection of 1×10$^6$ log phase cultured tumor cells (human MDA-MB468 breast or human HN5 head and neck carcinoma cells) suspended in 0.10 ml RPMI 1640. After sufficient time has elapsed for the tumors to become palpable. (2–3 mm in diameter) the test animals (athymic mice) are treated with compound (formulated by dissolution in DMSO typically at a concentration of 50 to 100 mg/mL followed by 1:9 dilution into 0.1% Pluronic® P105 in 0.9% saline) by the intraperitoneal (ip) or oral (po) routes of administration twice daily (i.e., every 12 hours) for 5 to 20 consecutive days. In order to determine an anti-tumor effect, the tumor is measured in millimeters with Vernier calipers across two diameters and the tumor size (mg) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother*. Results are expressed as percent inhibition, according to the formula: Inhibition (%)=(TuW$_{control}$−TuW$_{test}$)TuW$_{control}$×100%. The flank site of tumor implantation provides reproducible dose/response effects for a variety of chemotherapeutic agents, and the method of measurement (tumor diameter) is a reliable method for assessing tumor growth rates.

Administration of the compounds of this invention can be via any method which enables delivery of the compounds to the site of action (e.g., cancer cells). These methods include oral routes, intraduodenal routes, parenteral injection (including intravenous, subcutaneous, intramuscular, intravascular or infusion), topical administration, etc.

The amount of heteroaryl-fused pyrimidine derivative administered will, of course, be dependent on the subject being treated, on the severity of the affliction, on the manner of administration and on the judgement of the prescribing physician. However an effective dosage is in the range of approximately 0.1–100 mg/kg, preferably 1 to 35 mg/kg in single or divided doses. For an average 70 kg human, this would amount to 0.05 to 7 g/day, preferably 0.2 to 2.5 g/day.

The composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition or formulation to be administered will contain a quantity of a compound according to the invention in an amount effective to alleviate or reduce the signs in the subject being treated, i.e., proliferative diseases, over the course of the treatment.

Exemplary parenteral administration forms include solutions or suspensions of a compound according to the invention Formula I in sterile aqueous solutions, for example aqueous propylene glycol or dextrose solutions are employed. Such dosage forms can be suitably buffered, if desired.

Suitable pharmaceutical carriers include inert diluents or fillers, water and various organic solvents. These pharmaceutical compositions can, if desired, contain additional ingredients such as flavorings, binders, excipients and the like. Thus for oral administration, tablets containing various excipients, such as citric acid can be employed, together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials therefore include lactose or milk sugar and high molecular weight polyethylene glycols. When the aqueous suspensions or elixirs are desired for oral administration the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a certain amount of active ingredient are known, or will be apparent, to those skilled in this art. For examples, see Remington's Pharmaceutical Sciences., Mack Publishing Company, Easter, Pa., 15th Edition (1975).

The anticancer treatment described above may be applied as a sole therapy or may involve, in addition to the heteroaryl-fused pyrimidine derivative of the invention, one or more other antitumor substances. Such conjoint treatment may be achieved by way of the simultaneous, sequential, cyclic or separate dosing of the individual components of the treatment.

It should be understood that the invention is not limited to the particular embodiments shown and described herein, but that various changes and modifications may be made without departing from the spirit and scope of this novel concept as defined by the following claims.

EXAMPLE 1

(3-Ethynyl-phenyl)-(7H-pyrrolo[2,3-d]pyrimidin-4-yl)-amine Hydrochloride

To 4-chloro-7H-pyrrolo[2,3-d]pyrimidine (10.0 g, 0.065 mol) in dry pyridine (90 ml) was added m-aminophenylacetylene (9.2 g, 0.078 mol), and the mixture was heated in an 85° C. oil bath for 2 days. The reaction mixture was cooled to ambient temperature and concentrated in vacuo. The resulting residue was purified by flash chromatography on silica gel (375 g, 40 μm mesh) using 5% methanol/CH$_2$Cl$_2$ to afford the title compound as a pink-orange solid (1.9 g, 12%). HRMS: Calcd. 235.0984, Found 235.1000; anal. RP18-HPLC RT: 3.48 min.

The above compound was dissolved in a minimal amount of methanol and a solution of HCl in ethyl ether (HCl bubbled into 2 ml ethyl ether) was added dropwise until the mixture remained cloudy. The precipitated HCl salt was dried in vacuo, washed once with ethyl ether, and dried in vacuo to constant mass. MP: 196–198° C.

EXAMPLE 2

(3-Chloro-phenyl)-(7H-pyrrolo[2,3-d]pyrimidin-4-yl)-amine

Following the procedure described in Example 1, the title compound was prepared from 4chloro-7H-pyrrolo[2,3-d] pyrimidine and 3-chloroaniline (3.4%). LC-MS: 245 (MH$^+$); anal. RP18-HPLC RT: 3.74 min; HCl salt MP: 227–228° C.

EXAMPLE 3

4-(6-Chloro-2,3-dihydro-indol-1-yl)-7H-pyrrolo[2,3-d] pyrimidine Hydrochloride

Following the procedure described in Example 1, the title compound was prepared from 4-chloro-7H-pyrrolo[2,3-d] pyrimidine and 6-chloro-2,3-dihydroindol-1-yl (4.3%). HRMS: Calcd. 271.0750, Found 271.0729; anal. RP18-HPLC RT: 4.88 min; HCl salt MP: 266° C. (dec).

EXAMPLE 4

(7H-Pyrrolo[2,3-d]pyrimidin-4-yl)(-m-tolyl-)amine Hydrochloride

Following the procedure described in Example 1, the title compound was prepared from 4-chloro-7H-pyrrolo[2,3-d] pyrimidine and m-toluidine (34%). HRMS: Calcd. 225.1140, Found 225.1131; anal. RP18-HPLC RT: 3.45 min; HCl salt MP: 219° C.

EXAMPLE 5

(1H-indol-5-yl)-(7H-pyrrolo[2,3-d]pyrimidin-4-yl)-amine Hydrochloride

Following the procedure described in Example 1, the title compound was prepared from 4-chloro-7H-pyrrolo[2,3-d] pyrimidine and 5-aminoindole (7%). HRMS: Calcd. 250.1093, Found 250.1081; anal. RP18-HPLC RT: 2.58 min; HCl salt MP: 218–221° C.

EXAMPLE 6

Phenyl-(7H-pyrrolo[2,3-d]pyrimidin-4-yl)-amine

Utilizing a procedure analogous to that described in Example 1, this product was prepared in 16% yield from 4-Chloro-7H-pyrrolo[2,3-d]pyrimidine (1.0 eq) and aniline (5.0 eq) in pyridine. (M.P. 234–236° C.; GC-MS: 211(MH$^+$); anal. RP18-HPLC RT: 3.11 min.)

The compounds of Examples 7–10 were made according to the method of claim 6 from the appropriate starting materials.

| Ex. | R$^2$R$^3$N or R$^3$ | R$^2$ | Yield (%) | HPLC RT | LC/MS M+ |
|---|---|---|---|---|---|
| 7 | (6-methyl-indoline) | — | 23 | 4.62 | 251 |
| 8 | (benzothiophene) | H | 57 | 3.70 | 267 |
| 9 | (fluoro-chloro-indoline) | — | 23 | 4.66 | 289 |
| 10 | (indazole) | H | 71 | 2.23 | 251 |

EXAMPLE 11

1-(4-[m-Tolylamino]-1-(pyrrolo[2,3-d]pyrimidin-7-yl) ethanone Hydrochloride

To (3-methyl-phenyl)-(7H-pyrrolo [2,3-d]pyrimidin-4-yl)-amine (Example 4) (0.168 g, 0.75 mmol), dissolved in hot acetonitrile (7 ml), was added sodium hydride (36 mg, 0.90 mmol, 60% dispersion in mineral oil). After stirring at ambient temperature for 0.75 hours, acetyl chloride (0.11 ml, 1.5 mmol) was added.and stirring was continued for 48 hours. The mixture was concentrated in vacuo, triturated in hot ethyl acetate and filtered. The filtrate was concentrated in vacuo to give an orange solid residue. The solid was triturated in CH$_2$Cl$_2$ and filtered to afford the title compound as a light yellow solid (0.11 g, 55%). LC-MS: 267 (MH$^+$); anal. RP18-HPLC RT: 3.53 min.

EXAMPLE 12

(5-Iodo-7H-pyrrolo[2,3-d]pyrimidin-4-yl)-(m-tolyl)-amine

To 1-(4-tolylamino-pyrrolo[2,3-d]pyrimidin-7-yl)-ethanone (113 mg, 0.42 mmol), in dry methanol (4 ml), and CH$_2$Cl$_2$ (1 ml), was added Na$_2$CO$_3$ (45 mg, 0.42 mmol). After stirring at ambient temperature for 0.75 hours, N-iodosuccinimide (190 mg, 0.85 mmol) was added and stirring was continued for 48 hours. The mixture was concentrated in vacuo and partitioned between CH$_2$Cl$_2$ and H$_2$O. The organic phase was washed twice with H$_2$O, dried over Na$_2$SO$_4$ and concentrated in vacuo. The resulting residue was purified by flash chromatography on silica gel (7 g, 40 μm mesh) using 2% methanol/CH$_2$Cl$_2$ to afford the title compound as olive needles (6 mg, 4%). LC-MS: 351 (MH$^+$); anal. RP18-HPLC RT: min.

EXAMPLE 13

(3-Chloro-phenyl)-(1H-[1,2,3]triazolo[4,5-d]pyrimidin-7-yl)-amine Hydrochloride

To 3-chloroaniline (0.39 ml, 3.6 mmol) in dry dimethyl-cyclohexylamine (0.55 ml, 3.6 mmol) was added phosphorus pentoxide (0.52 g, 3.6 mmol). After heating in a 170° C. oil bath for 0.5 hours, 8-azahypoxanthine (0.50 g, 3.6 mmol) was added and stirring continued at 170° C. for 23 hours. The mixture was cooled to ambient temperature and 2M NaOH was added until basic. The solids were filtered off and washed consecutively with H$_2$O, CH$_2$Cl$_2$ and methanol. The resulting solid was dried in vacuo to afford the title compound as a tan powder (0.26 g, 29%). LC-MS: 247 (MH$^+$); anal. RP18-HPLC RT: 3.76 min.

EXAMPLE 14

(3Chloro-phenyl)-(pyrido[4,3-d]pyrimidin-4-yl)-amine Hydrochloride

To 4-hydroxy-pyrido[4,3-d]pyrimidine (0.13 g, 0.90 mmol) in phosphorus oxychloride (2 ml) was added dry pyridine (0.15 ml, 1.8 mmol). A condenser and CaCl$_2$ drying tube were attached and the suspension was refluxed for 3 hours. The final, clear solution was concentrated in vacuo (CaCl$_2$ drying tube) and followed by a toluene chase. The resulting 4-chloro-pyrido[4,3-d]pyrimidine was dissolved in dry pyridine (1.5 ml). 3-Chloroaniline (0.096 ml, 0.90 mmol) was added, and the mixture was heated in an 85° C. oil bath for 23 hours. The reaction was cooled to ambient temperature and concentrated in vacuo. The oily residue was partitioned between CH$_2$Cl$_2$ and H$_2$O, filtered, and the H$_2$O phase extracted with CH$_2$Cl$_2$. The combined organic phases were dried over Na$_2$SO$_4$ and concentrated in vacuo. The resulting residue was purified by flash chromatography on silica gel (5 g, 40 μm mesh) using 5% methano/CH$_2$Cl$_2$ to afford the title compound as an off-white solid (3 mg, 1.3%). LC-MS: 257 (MH$^+$); anal. RP18-HPLC RT: 3.85 min.

EXAMPLE 15

(1H-Indol-5-yl)-(pyrido[4,3-d]pyrimidin-4-yl)-amine Hydrochloride

To a suspension of 4-hydroxy-pyrido[4,3-d]pyrimidine (0.103 g, 0.70 mmol) in dry pyridine (2 ml) cooled in an ice-water bath was added dropwise trifluoroacetic anhydride (0.20 ml, 1.4 mmol). After stirring for 0.5 hours, a solution of 5-aminoindole (0.204 g, 1.5 mmol) in dry dimethylformamide (DMF) (1.5 ml) was added dropwise. The cold bath was allowed to warm to ambient temperature and stirring continued for 24 hours. The mixture was concentrated in vacuo and partitioned between $CH_2Cl_2$ and $H_2O$. The $H_2O$ phase was extracted with $CH_2Cl_2$, and the combined organic phases washed with $H_2O$, dried over $Na_2SO_4$ and concentrated in vacuo. The resulting residue was purified by flash chromatography on silica gel (11 g, 40 μm mesh) using 5% methanol/$CH_2Cl_2$ to afford the title compound as an orange solid (37 mg, 20%). LC-MS: 262 (MH$^+$); anal. RP18-HPLC RT: 2.02 min.

EXAMPLE 16

(3-Ethynylphenyl)-(7-methyl-pyrido[4,3-d]pyrimidin-4-yl)-amine Hydrochloride

Utilizing a procedure analogous to that described in Example 16, this product was prepared in 28% yield from 4-hydroxy-7-methyl-pyrido[4,3-d]pyrimidine (1.0 eq) and m-aminophenyl acetylene (40.0 eq) in pyridine. The HCl salt was prepared from the purified free base according to/the procedure given in Example 1. (M.P. 240–241° C.; GC-MS: 261 (MH$^+$); anal. RP18-HPLC RT: 3.73 min.)

EXAMPLE 17

(3-Chloro-phenyl)-(7-methyl-pyrido[4,3-d]pyrimidin-4-yl)-amine Hydrochloride

Utilizing a procedure analogous to that described in Example 16, this product was prepared in 34% yield from 4-hydroxy-7-methyl-pyrido[4,3-d]pyrimidine (1.0 eq) and m-chloroaniline (40.0 eq) in pyridine. The HCl salt was generated from the purified free base according to the procedure given in Example 1. (M.P. 255–256° C.; GC-MS: 270 (MH$^+$); anal. RP18-HPLC RT: 4.05 min.)

EXAMPLE 18

(3-Ethynyl-phenyl)-(pyrido[4,3-d]pyrimidin-4-yl)-amine Hydrochloride

Following the procedure described in Example 16, the title compound was prepared from 4-hydroxy-pyrido[4,3-d]pyrimidine and m-aminophenyl acetylene (5%). LC-MS: 247 (MH$^+$); anal. RP18-HPLC RT: 3.41 min.

The compounds of Examples 19–24 were made according to the method of Example 20 from the appropriate starting materials.

| Ex. | $R^2R^3N$ or $R^3$ | $R^2$ | Yield (%) | HPLC RT | LC/MS M+ |
|---|---|---|---|---|---|
| 19 | 5-F, 6-Br indoline | — | 45 | 3.64 | 359 |
| 20 | 5-Cl, 6-F indoline | — | — | — | 315 |
| 21 | 1H-indazol-5-yl | H | — | — | 277 |
| 22 | 4-HO, 3-methyl phenyl | H | — | — | 267 |
| 23 | 6-I indoline | — | — | — | 389 |
| 24 | benzothiophen-5-yl | H | 55 | 3.44 | 341 |

EXAMPLE 25

(3-Ethynyl-phenyl)-(9H-purin-6-yl)-amine

To 6-chloropurine (1.0 g, 6.5 mmol) in dry pyridine (10 ml) was added m-aminophenyl acetylene (0.91 g, 7.8 mmol). The mixture was heated in an 85° C. oil bath for 23 hours. The mixture was cooled to ambient temperature and concentrated in vacuo. The oily residue was partitioned between $CH_2Cl_2$ and $H_2O$ then filtered to afford the title compound as a light orange solid (50 mg, 3.3%). LC-MS: 236 (MH$^+$); anal. RP18-HPLC RT: 3.25 min.

EXAMPLE 26

(1H-Indol-5-yl)-(9H-purin-6-yl)-amine Hydrochloride

Following the procedure described in Example 9, the title compound was prepared from 6-chloropurine and 5-aminoindole (70%). TS-MS: 251 (MH+); anal. RP18-HPLC RT: 2.44 min.

EXAMPLE 27
(3-Chloro-phenyl)-(9H-purin-yl)-amine Hydrochloride

Following the procedure described in Example 1, the title compound was prepared from 4chloro-7H-pyrrolo[2,3-d]pyrimidine and 3-chloroaniline (3.4%). LC-MS: 245 (MH+); anal. RP18-HPLC RT: 3.74 min; HCl salt MP: 227–228° C.

EXAMPLE 28
4-(6-Chloro-2,3-dihydro-indol-1-yl)-pyrido[3,4-d]pyrimidine

4-Chloropyrido[3,4]pyrimidine (0.10 g, 0.60 mmol), 6-chloroindoline (0.10 g, 0.66 mmol) and pyridine (0.14 g, 1.81 mmol) were combined in DMF (1 mL) and heated at 70° C. for 3 hr. The reaction was cooled to room temperature and then added to methylene chloride (150 mL). The organic layer was washed with saturated sodium carbonate and water and then dried over sodium sulfate. The solvent was removed by rotary evaporation and the residue purified by column chromatography (silica gel, 9/2/1—$CH_2Cl_2$/hexanes/methanol) to give a pale yellow residue (0.048 g, 28%). MP 194–6° C.; LCMS: 283 (MH+).

The products of examples 29–31 were prepared according to the method of Example 1 from 4-chloropyrido[3,4-d]pyrimidine (1 eq.) and the indicated amine.

EXAMPLE 29
Pyrido[3,4-d]pyrimidin-4-yl-m-tolyl-amine

This product was prepared in 44% yield from m-anisidine (1.1 eq.) MP 172° C.; LC-MS: 237 (MH+).

EXAMPLE 30
(1H-Indazol-5-yl):pyrido[3,4-d]pyrimyidin-4-yl-amine

This product was prepared in 96% yield from 5-aminoindazole (1.1 eq.) MP 258° C.; LC-MS: 263 (MH+).

EXAMPLE 31
(1H-Indol-5-yl)-pyrido[3.4-d]pyrimidin-4-yl-amine

This product was prepared in 15% yield from 5-aminoindole (1.1 eq.) 4-chloropyrido[3,4-d]pyrimidine (1 eq.) MP 265° C.; LC-MS: 262 (MH+).

EXAMPLE 32
Phenyl-pyrido[2,3-d]pyrimidin-4-yl-amine

4-Chloropyrido [2,3-d]pyrimidine (0.15 g, 0.91 mmol) was carefully added to a solution of aniline (0.15 g, 1.61 mmol) on water (1.5 mL). The solution was heated for 0.5 hour on a steam bath, cooled, and then basified with conc. ammonium hydroxide. The crude precipitate was collected by filtration and recrystallized from 95% ethanol to give the title product as yellow crystals (0.054 g, 27%). MP 258° C.; LC-MS: 223 (MH+).

The products of Examples 33–36 were prepared according to the procedure of Example 5 from 4-chloropyrido[2,3-d]pyrimidine (1 eq.) and the appropriate substituted aniline.

EXAMPLE 33
(3Chloro-phenyl-pyrido[2,3-d]pyrimidin-4-yl-amine

This product was prepared in 61% yield from m-chloroaniline (1.8 eq.). MP 228° C.; LC-MS: 257 (MH+).

EXAMPLE 34
(3-Chloro-phenyl-pyrido[3,4-d]pyrimidin-4-yl-amine

This product was prepared in 37% yield from m-chloroaniline (1.8 eq.). MP 228° C.; LC-MS: 257 (MH+).

EXAMPLE 35
(3-Bromo-phenyl-pyrido[3,4-d]pyrimidin-4-yl-amine

This product was prepared in 26% yield from m-bromoaniline (1.8 eq.). MP 206° C.; LC-MS: 301 (MH+).

EXAMPLE 36
Phenyl-pyrido[3,4-d]pyrimidin-4-yl-amine

This product was prepared in 22% yield from aniline (1.8 eq.). MP 161° C.; LC-MS: 223 (MH+).

EXAMPLE 37
4-(6-Chloro-2,3-dihydro-indol-1-yl)-pyrido[3,4-d]pyrimidine

4-Chloropyrido[3,4-d]pyrimidine (0.10 g, 0.60 mmol), 6-chloroindoline (0.10 g, 0.66 mmol) and pyridine (0.14 g, 1.81 mmol) were combined in DMF (1 mL) and heated at 70° C. for 3 hours. The reaction was cooled to room temperature and then added to methylene chloride (150 mL). The organic layer was washed with saturated sodium carbonate and water and then dried over sodium sulfate. The solvent was removed by rotary evaporation and the residue purified by column chromatography (silica gel, 9/2/1—$CH_2Cl_2$/hexanes/methanol) to give the title product as a pale yellow residue (0.048 g, 28%). MP 194–6° C.; LCMS: 283 (MH+).

EXAMPLE 38
(Pyrido[3,4-d]pyrimidin-4-yl)-m-tolyl-amine

This product was prepared in 44% yield from m-anisidine (1.1 eq.) MP 172° C.; LC-MS: 237 (MH+).

The products of Examples 39–40 were prepared according to the procedure of Example 1 from 4-chloropyrido[3,4-d]pyrimidine (1 eq.) and the appropriate amine.

EXAMPLE 39
(1H-Indazol-5-yl)-pyrido[3,4-d]pyrimidin-4-yl-amine

This product was prepared in 96% yield from 5-aminoindazole (1.1 eq.) and 4-chloropyrido[3,4-d]pyrimidine (1 eq.). MP 258° C.; LC-MS: 263 (MH+).

EXAMPLE 40
(1H-Indol-5-yl)pyrido[3,4-d]pyrimidin-4-yl-amine

This product was prepared in 15% yield from 5-aminoindole (1.1 eq.) and 4-chloropyrido[3,4-d]pyrimidine (1 eq.). MP 265° C.; LC-MS: 262 (MH+).

EXAMPLE 41
Phenyl-pyrido[2,3-d]pyrimidin-4-yl-amine

4-Chloropyrido [2,3-d]pyrimidine (0.15 g, 0.91 mmol) was carefully added to a solution of aniline (0.15 g, 1.61 mmol) in water (1.5 mL). The solution was heated for 0.5 h on a steam bath, cooled, and then basified with conc. ammonium hydroxide. The crude precipitate was collected by filtration and recrystallized from 95% ethanol to give yellow crystals (0.054 g, 27%). MP 258° C.; LC-MS: 223 (MH+).

EXAMPLE 42
(3-Chloro-phenyl-pyrido[2,3-d]pyrimidin-4yl-amine

Using a procedure analogous to that described in Example 5, this product was prepared in 61% yield from m-chloroaniline (1.8 eq.) and 4-chloropyrido[2,3-d]pyrimidine (1 eq.). MP 228° C.; LC-MS: 257 (MH+).

EXAMPLE 43
(3-Chloro-phenyl-pyrido[3,4-d]pyrimidin-4-yl-amine

Using a procedure analogous to that described in Example 5, this product was prepared in 37% yield from m-chloroaniline (1.8 eq.) and 4-chloropyrido[3,4-d]pyrimidine (1 eq.). MP 228° C.; LC-MS: 257 (MH+).

EXAMPLE 44
(3-Bromo-phenyl-pyrido[3,4-d]pyrimidin-4-yl-amine

Using a procedure analogous to that described in Example 5, this product was prepared in 26% yield from m-bromoaniline (1.8 eq.) and 4-chloropyrido[3,4-d]pyrimidine (1 eq.). MP 206° C.; LC-MS: 301 (MH+).

EXAMPLE 45
Phenyl-pyrido[3,4-d]pyrimidin-yl-amine

Using a procedure analogous to that described in Example 5, this product was prepared in 22% yield from aniline (1.8 eq.) and 4-chloropyrido[3,4-d]pyrimidine (1 eq.). MP 161° C.; LC-MS: 223 (MH+).

EXAMPLE 46
(7-Benzenesulfonyl-7H-pyrrolo[2,3-d]pyrimidin-4-yl-(3-ethynyl-phenyl)-amine To 4-chloro-7H-pyrrolo[2,3-d]pyrimidine (1.0 g, 0.0065 mol) in dry THF (10 ml) under nitrogen at −78° C. was added dropwise via syringe over 15 minutes n-butyllithium (2.5 M in hexane; 2.88 ml, 0.0072 mol). The cooling bath was removed and the solution was stirred for 1 hour. The resulting pyrrolo anion salt precipitated as a very fine white solid in a cloudy colorless solution. After the suspension was recooled to −78° C., benzenesulfonyl chloride (1.26 g, 0.0072 mol) was added neat via syringe. The resulting yellow reaction mixture was allowed to warm slowly to room temperature overnight. The grey-white suspension was poured into 2% aqueous sodium bicarbonate (50 mL) and extracted with two times with diethyl ether (2 mL). The combined extracts were washed with water and dried (potassium carbonate) and evaporated to give a light amber oil which crystallized from ether, the product was collected by filtration to 1.4 g (74%) of white solid. LC-MS=294 (MH+) RP18-HPLC RT: 4.40 min.

The above compound was dissolved in methanol and m-aminophenyl acetylene (0.159 g, 0.0013 mol), and the reaction mixture heated in an 85° C. oil bath for 2 days. The reaction mixture was cooled to ambient temperature and concentrated in vacuo. The residue was titurated with diethyl ether to produce the title product as a white solid (0.234 g, 92%). LC-MS=375 (MH+), RP18-HPLC RT: 3.48 min.

EXAMPLE 47
4-(6-Chloro-2,3-dihydro-indol-1-yl)-5H-pyrrolo[3,2-d]pyrimidin-6-ol To a solution of 4-(6-Chloro-2,3-dihydro-indol-1-yl)-5-amino-6-methylacetylpyrimidine (541 mg, 1.55 mmol) in 40 mL of ethanol was added 25 mol % of 10% palladium on carbon (125 mg) and 0.11 mL of 1N HCl (1.55 mmol). The reaction mixture was hydrogenated for 3 hours at 50 psi. The reaction mixture was filtered through Celite and concentrated in vacuo. The brown residue was slurried in methanol and the white solid title product was filtered off (279 mg, 63%)LC-MS=287 (M+), RP18-HPLC RT: 5.61 min. MP: 250° C.(dec).

EXAMPLE 48
(3-Ethynyl-phenyl)-[7-(2-morpholin-4-yl-ethyl)-7H-pyrro[2,3-d]pyrimidin-4-yl]-amine To a solution of 184 mg (1.4 mmol) of 4-(2-hydroxyethyl)morpholine in 10 mL of toluene was added 276 mg (2.0 mmol) of anhydrous potassium carbonate and then 32 mg (1.3 mmol) of 97% sodium hydride. After 30 minutes 343 mg (1.0 mmol) of sulfonylated 4-chloro-7H-pyrrolo[2,3-d]pyrimidine was added and the reaction mixture was heated at 100° C. for 2 hours. The reaction mixture was then partitioned between ethyl acetate and water and the aqueous layer was extracted with two additional portions of ethyl acetate. The combined organic phases were washed with water, dried over magnesium sulfate and concentrated in vacuo. The residue was chromatographed on silica gel using 10% methanol/methylene chloride to give an amber oil (140 mg, 55%). LC-MS 267 (M+)

The above product was dissolved in methanol and m-aminophenyl acetylene (0.123 g, 0.001 mol), and the reaction mixture was heated in a sealed tube in a 120° C. oil bath for 12 hours. The reaction mixture was cooled to ambient temperature and concentrated in vacuo. The residue was titurated with diethyl ether to produce the title product as a white solid (0.135 g, 74%). LC-MS=348 (MH+), RP18HPLC RT: 3.33 min.

EXAMPLE 49
(3-Ethynyl-phenyl)-[7-(2-methoxy-ethyl)-7H -pyrrolo[2,3-d]pyrimidine-4-yl-]-amine Utilizing a procedure analogous to that described in Example 47, this product was prepared in 81% yield from 4-chloro-7-(2-methoxy-ethyl)-7H-pyrrolo[2,3-d]pyrimidine (1.0 eq) and m-aminophenyl acetylene (1.2 eq) in methanol. M.P. 240–241° C.; LC-MS: 292(MH+); RP18-HPLC RT: 4.16 min.

EXAMPLE 50
(3-Ethynyl-phenyl)-{7-[2-(2-methoxy-ethoxy)-ethyl]-7H-pyrrolo[2,3-d]pyrimidin-4-yl}-amine Utilizing a procedure analogous to that described in Example 47, this product was prepared in 81% yield from 4-chloro-7-[2-(2-methoxy-ethoxy)-ethyl]-7H-pyrrolo[2,3-d]pyrimidine (1.0 eq) and m-aminophenyl acetylene (1.2 eq) in methanol. M.P. 240–241° C.; LC-MS: 336 (M+); RP18HPLC RT: 4.29 min.

EXAMPLE 51
(7-Allyl-pyrrolo[2,3-d]pyrimidin-4-yl)-(3-ethynyl-phenyl)-amine Hydrochloride To 4-chloro-7H-pyrrolo[2,3-d]pyrimidine (1.3 g, 8.5 mmol) in dry THF (30 ml) was added sodium hydride (1.0 g, 0.25 mmol, 60% dispersion in mineral oil). After stirring at ambient temperature for 1 hour, allyl iodide (0.93 ml, 10 mmol) was added and stirring was continued for 48 hours. The reaction mixture was concentrated in vacuo, triturated in hot ethyl acetate, and filtered. The filtrate was concentrated in vacuo to give an orange solid residue. The solid was triturated in methylene chloride and filtered to afford 4-chloro-7-allyl-pyrrolopyrimidine as a light yellow powder (0.58 g, 36%). TS-MS: 194 (MH+); anal. RP18HPLC RT: min.

To 4-chloro-7-allyl-pyrrolopyrimidine (0.5 g, 2.6 mmol) in dry methanol (5 ml) was added m-aminophenyl acetylene (0.36 g, 3.1 mmol). The suspension was heated in a sealed pressure tube at 125° C. for 20 hours. The reaction mixture was cooled to ambient temperature and concentrated in vacuo. The resulting oil was purified by flash chromatography on silica gel (50 g, 40 mm mesh) using 3% methanol/methylene chloride to afford the title product as a yellow powder (0.29 g, 41% ). TS-MS: 275 (MH+); anal. RP18-HPLC RT: min.

EXAMPLE 52
(3-Ethynyl-phenyl)-(7-methyl-pyrrolo[2,3-d]pyrimidin-4-yl)-amine Hydrochloride Following the procedure described in Example 1, the title compound was prepared from 4-chloro-7H-pyrrolo[2,3-d]

pyrimidine and methyl iodide, and m-aminophenyl acetylene (75%). TS-MS: 249 (MH+); anal. RP18-HPLC RT: min.

EXAMPLE 53
(5-Bromo-7H-pyrrolo[2,3-d]pyrimidin-4-yl)-(3-ethynyl-phenyl)-amine To 4-chloro-7H-pyrrolo[2,3-d]pyrimidine (0.21 g, 1.4 mmol) in dry methylene chloride (10 ml) was added N-bromosuccinimide (0.26 g, 1.5 mmol) at ambient temperature. The reaction mixture was stirred for 18 hours, and the resulting solid filtered with methylene chloride washes and dried in vacuo to afford 5-bromo-4-chloro-7H-pyrrolo[2,3-d]pyrimidine as a tan powder (0.28 g, 88%). GC-MS: 233 (MH+), RT: 4.42 min.

To 5-bromo-4-chloro-7H-pyrrolo[2,3-d]pyrimidine (0.13 g, 0.57 mmol) in dry methanol (2 ml) was added m-aminophenyl acetylene (0.08 g, 0.68 mmol). The suspension was heated in a sealed pressure tube at 125° C. for 18 hours. The reaction mixture was cooled to ambient temperature and concentrated in vacuo. The resulting oil was purified by flash chromatography on silica gel (10 g, 40 mm mesh) using 3% methanol/methylene chloride to afford the title compound as a yellow powder (71 mg, 39%). TS-MS: 314 (MH+); anal. RP18-HPLC RT: min.

EXAMPLE 54
(3-Ethynyl-phenyl)-(5-iodo-7H-pyrrolo[2,3-d]pyrimidin-4-yl)-amine To (3-methyl-phenyl)-(7H-pyrrolo[2,3-d]pyrimidin-4-yl)amine (17mg, 0.076 mmol) in dry methylene chloride (1 ml) was added N-iodosuccinimide (19 mg, 0.083 mmol). The reaction mixture was stirred at ambient temperature for 2 hours then filtered with a methylene chloride wash and dried in vacuo to afford the title compound as a grey-tan powder (12 mg, 46%). TS-MS: 351 (MH+); anal. RP18-HPLC RT: min.

EXAMPLE 55
4-(3-Ethynyl-phenylamino)-7H-pyrrolo[2,3-d]pyrimidine-5-carboxylic Acid To 5-bromo-4-chloro-7H-pyrrolo[2,3-d]pyrimidine (0.87 g, 3.7 mmol) in dry THF (29 ml) cooled in a dry ice-acetone bath was added dropwise n-butyllithium (3.4 ml, 8.4 mmol, 2.5 M in hexanes). The reaction mixture was stirred for 1 hour then quenched by bubbling in $CO_2$. To the resulting olive suspension was added water (1 ml) and stirred for 5 minutes at ambient temperature. The reaction mixture was concentrated in vacuo, triturated with ethyl acetate, and dried in vacuo to afford 4-chloro-7H-pyrrolo[2,3-d]pyrimidine-5-carboxylic acid as an avocado powder (0.80 g, 74%). TS-MS: 198 (MH+); anal. RP18-HPLC RT: min.

To 4-chloro-7H-pyrrolo[2,3-d]pyrimidine-5-carboxylic acid (0.38 g, 1.9 mmol) in dry methanol (4ml) was added m-aminophenyl acetylene (0.47 g, 4.0 mmol). The suspension was heated in a sealed pressure tube at 125° C. for 18 hours. The reaction mixture was cooled to ambient temperature, filtered with methylene chloride washes and dried in vacuo to afford the title compound as a tan powder (0.30 g, 54%). TS-MS: 278 (MH+); anal. RP18-HPLC RT: min.

EXAMPLE 56
(3-Ethynyl-phenyl)-(5-methyl-7H-pyrrolo[2,3-d]pyrimidin-4-yl)-amine Hydrochloride To 5-bromo-4-chloro-7H-pyrrolopyrimidine (0.28 g, 1.2 mmol) in dry THF (9 ml) cooled in a dry ice-acetone bath was added dropwise n-butyllithium (1.1 ml, 2.7 mmol, 2.5 M in hexanes). The reaction mixture was stirred for 1 hour, then methyl iodide (0.12 ml, 1.9 mmol) was added. The solution was stirred for 1 hour at ambient temperature, and water (1 ml) was added. The reaction mixture was concentrated in vacuo, and diluted with ethyl acetate and water. The organic phase was washed twice with water, dried over sodium sulfate, and concentrated in vacuo to afford 4-chloro-5-methyl-7H-pyrrolo[2,3-d]pyrimidine (0.17 g, 85%). GC-MS: 167(M+), RT: 3.15 min.

To 4-chloro5-methyl-7H-pyrrolopyrimidine (0.17 g, 1.0 mmol) in dry methanol (3 ml) was added m-aminophenyl acetylene (0.14 g, 1.2 mmol). The suspension was heated in a sealed pressure tube at 125° C. for 18 hours. The reaction mixture was cooled to ambient temperature, and concentrated in vacuo. The resulting residue was purified by flash chromatography on silica gel (15 g,40 mm mesh) using 5% methanol/methylene chloride to afford the title compound as a yellow solid (0.11 g, 43%). TS-MS: 249 (MH+); anal. RP18-HPLC RT: min.

EXAMPLE 57
N-(5-Iodo-7H-pyrrolo[2,3-d]pyrimidin-4-yl)-N-m-tolyl-acetamide

To (3-methyl-phenyl)-(7H-pyrrolo[2,3-d]pyrimidin-4-yl)-amine (0.75 g, 3.4 mmol) dissolved in hot acetonitrile (30 ml) was added sodium hydride (0.16 g, 4.0 mmol, 60% dispersion in mineral oil). After stirring at ambient temperature for 0.75 hours, acetyl chloride (0.48 ml, 6.7 mmol) was added and stirring continued for 48 hours. The reaction mixture was concentrated in vacuo, triturated in hot ethyl acetate, and filtered. The filtrate was concentrated in vacuo to give an orange solid residue. The solid was purified by flash chromatography on silica gel (13 g,40 mm mesh) using 1:3 ethyl acetate/hexanes to afford 1-(4-m-tolylamino-pyrrolo[2,3-d]pyrimidin-7-yl)-ethanone as a yellow solid (0.21 g). TS-MS: 309 (MH+); anal. RP18-HPLC RT: min.

To 1-(4-m-tolylamino-pyrrolo[2,3-d]pyrimidin-7-yl) ethanone (0.21 g, 0.79 mmol) in dry methylene chloride (5 ml) and dry methanol (2 ml) was added sodium carbonate (0.17 g, 1.6 mmol). After stirring at ambient temperature for 0.75 hours, N-iodosuccinimide (0.35 g, 1.6 mmol) was added. The reaction mixture was stirred at ambient temperature for 48 hours then concentrated in vacuo. The residue was diluted with methylene chloride and water. The water phase was extracted once with methylene chloride. The organic phase was washed twice with water, dried over sodium sulfate, and concentrated in vacuo. The resulting residue was purified by flash chromatography on silica gel (11 g, 40 mm mesh) using 2% methanol/methylene chloride to afford the title compound as a yellow solid (30 mg). TS-MS: 393 (MH+); anal. RP18-HPLC RT: min.

EXAMPLE 58
4-(3-Ethynyl-phenylamino)-7H-pyrrolo[2,3-d]pyrimidine-5-carboxylic Acid Methyl Ester Hydrochloride To 4-(3-ethynyl-phenylamino)-7H-pyrrolo[2,3-d]pyrimidine-5-carboxylic acid (0.108 g, 0.39 mmol) in dry methylene chloride (2 ml) was added a solution of oxalyl chloride (0.17 ml, 1.9 mmol) in dry methylene chloride (4 ml) followed by 1 drop of dry DMF. The suspension was stirred at ambient temperature for 1 hour, then concentrated in vacuo. To the resulting solid was added dry acetone (2 ml) and dry methanol (1 ml). The solution was stirred at ambient temperature for 15 hours, then concentrated in vacuo. The residue was diluted with ethyl acetate and water, and the solid filtered and dried in vacuo to afford the title compound as a tan powder (40 mg, 35%). TS-MS: 293 (MH+); anal. RP18-HPLC RT: min.

EXAMPLE 59

(3-ethynyl-phenylamino)-(7H-pyrrolo[2,3-d]pyrimidin-5-yl-carbonitrile

To 5-bromo-4-chloro-7H-pyrrolo[2,3-d]pyrimidine (0.31 g, 1.3 mmol) in dry THF (4 ml), cooled in a dry ice-acetone bath, was added dropwise n-butyllithium (1.3 ml, 3.3 mmol, 2.5 M In hexanes). The reaction mixture was stirred for 1 hour, then p-toluenesulphenyl cyanide (0.44 g, 2.4 mmol) suspended in dry THF (7 ml) was added. The solution was stirred for 18 hours at ambient temperature then diluted with aqueous ammonium chloride. The phases were separated and the organic phase washed with water and aqueous NaCl. The organic phase was dried over sodium sulfate, and concentrated in vacuo. The resulting residue was purified by flash chromatography on silica gel (15 g, 40 mm mesh) using 3% methanol/methylene chloride to afford 4-chloro5-cyano-7H-pyrrolo[2,3-d]pyrimidine as a yellow solid (52 mg).

To 4-chloro-5-cyano-7H-pyrrolo[2,3-d]pyrimidine (52 mg, 0.29 mmol) in dry methanol (3 ml) was added m-aminophenyl acetylene (41 m g, 0.35 mmol). The suspension was heated in a sealed pressure tube at 125° C. for 18 hours. The reaction mixture was cooled to ambient temperature, filtered with a small amount of methanol, and dried in vacuo to afford the title compound as a white solid (27 mg, 36%). TS-MS: 260 (MH+); anal. RP18-HPLC RT: 3.70 min.

EXAMPLE 60

(1-Indazol-5-yl)-(6-methyl-pyrido[3,4-d]pyrimidin-4-yl)-amine Hydrochloride

6-Methyl-pyrido[3,4-d]pyrimid-4-one (200 mg, 1.24 mmol), polymer-supported triphenylphosphine (2.06 g of about 3.0 mmol P/g resin, 6.20 mmol) and anhydrous carbon tetrachloride (1.20 mL, 12.40 mmol) were combined in 1,2-dichloroethane (6 mL). The reaction mixture was heated to 60° C. under an atmosphere of dry nitrogen for 18 hours. 5-Aminoindazole (221 mg, 1.66 mmol) was added and heating was continued at 60° C. for another 18 hours. The triphenylphosphine-supporting polymer was filtered off and washed several times with chloroform. The filtrate and washings were concentrated in vacuo, and flash chromatographed on silica in 10% methanol/0.1% triethylamine/89.9% methylene chloride to afford 207 mg of the free base of the title product (LC-MS: 277(MH+). This material was dissolved in a minimum volume of chloroform and 1 mole equivalent of HCl in ether was added dropwise with stirring. The reaction mixture was diluted with ether (4volumes) and the precipitated HCl salt of the title product was filtered and dried in vacuo (188 mg; M.P. 208° C.; LC-MS: 277 (MH+); anal. RP-HPLC: 2.71 min.)

EXAMPLE 61

Benzo[b]thiophen-5-yl-(6-methyl-pyrido[3,4-d]pyrimidin-4-yl)-aminehydrochloride

This material was prepared from 6-methyl-pyrido[3,4-d]pyrimid -4-one (1.0 eq.) and 5-amino-benzo[b]thiophene (1.5 eq.) as described for Example 60. The polymer was filtered off and washed several times with 30% methanol/70% chloroform. Triethylamine (3.0 eq) was added to the filtrate and washings before they were concentrated in vacuo. The residue was flash chromatographed on silica in 10% methanol/methylenechloride to afford 135 mg of product as the free base (LC-MS: 293(MH+)). This material was dissolved in a minimum volume of chloroform and 1 mole equivalent of HCl in ether was added dropwise with stirring. The reaction mixture was diluted with ether (4volumes) and the precipitated title product was filtered and dried in vacuo (152 mg; M.P. 273–276° C.; LC-MS: 293 (MH+); anal. RP-HPLC:4.10 min.).

EXAMPLE 62

(3-Ethynyl-4-fluoro-phenyl)-(6-methyl-pyrido[3,4-d]pyrimidin-4-yl)-amine

6Methyl-pyrido[3,4-d]pyrimid-4-one (44 mg, 0.27 mmol), polymer -supported triphenylphosphine (0.462 g of about 3.0 mmol P/g resin, 1.55 mmol) and anhydrous carbon tetrachloride (0.261 mL, 2.71 mmol) were combined in 1,2-dichloroethane (1.25 mL). The reaction mixture was heated to 60° C. under an atmosphere of dry nitrogen for 2 hours. 3-Ethynyl-4-fluoro-aniline (55 mg, 0.407 mmol) was added and heating was continued at 60° C. for 6 hours. The polymer was filtered off and washed several times with 50% methanol/chloroform. The filtrate and washings were concentrated in vacuo and flash chromatographed on silica with gradient from 0 to 10% methanol/methylene chloride to afford the title product (10 mg; M.P. 225° C.; LC-MS: 279 (MH+); anal. RP-HPLC: 3.94 min.).

EXAMPLE 63

2-Methyl-4-(6-methyl-pyrido[3,4-d]pyrimidin -4-ylamino)-phenol Dihydrochloride

This material was prepared from 6-methyl-pyrido[3,4-d]pyrimid-4-one (1.0 eq.) and 4-amino-o-cresol (1.5 eq.) as described for Example 61. The triphenylphosphine-supporting polymer was filtered off and washed several times with 50% methanol/chloroform. Triethylamine (3.0 eq) was added to the filtrate before concentrating in vacuo. The residue was flash chromatographed on silica with gradient from 0 to 15% methanol/methylene chloride to afford 314 mg of title product as the free base (LC-MS: 267(MH+). This material was converted to the dihydrochloride salt by dissolution in CHCl$_3$ and titration with 2 equivalents of 1M HCl in ether. The precipitated title product was filtered and dried in vacuo (M.P. 298–305° C.; LC-MS: 267 (MH+); anal. RP-HPLC: 2.88 min.).

EXAMPLE 64

4-(4-Bromo-7-methyl-2,3-dihydro-indol-1-yl)-6-methyl-pyrido[3,4-d]pyrimidine Hydrochloride This product was prepared from 6-methyl-pyrido[3,4-d]pyrimid-4-one (1.0 eq.) and 4-bromo-7-methyl-7-indoline (1.5 eq.) according to the procedure described for Example 61. The crude product from the filtrate was flash chromatographed on silica using ethyl acetate/hexanes/methanol (9:2:1) to afford the free base of the title product which was converted to the title product as described for Example 60 (33%; M.P. 232–244° C.; LC-MS: 355, 357 (MH+); anal. RP-HPLC: 5.20 min.).

EXAMPLE 65

4-(6-Bromo-7-methyl-2,3-dihydro-indol-1-yl)-6-methyl-pyrido[3,4-d]pyrimidine Hydrochloride This product was prepared from 6-methyl-pyrido[3,4-d]pyrimid-4-one (1.0 eq.) and 6-bromo-7-methyl-indoline (1.5 eq.) according to the procedure described for Example 61. The crude product from the filtrate was flash chromatographed on silica using ethyl acetate/hexanes/methanol (9:2:1) to afford the free base of the title product which was converted to the title product salt as described for Example 60 (34%; M.P. 212–229° C.; LC-MS: 355, 357 (MH+); anal. RP-HPLC:4.90 min.).

EXAMPLE 66
4-(6-Bromo-5-fluoro-2,3-dihydro-indol-1-yl)-6-methyl-pyrido[3,4-d]pyrimidine Hydrochloride This product was prepared from 6-methyl-pyrido[3,4-d]pyrimid-4-one (1.0 eq.) and 6-bromo-5-fluoro-indoline (1.5 eq.) according to the procedure described for Example 61. The crude product from the filtrate was flash chromatographed on silica using 2% methanol/98% methylene chloride to afford the free base of the title product which was converted to the title product as described for Example 60 (36%; M.P. 262–264° C.; LC-MS: 359, 361 (MH+); anal. RP-HPLC:4.83 min.).

EXAMPLE 67
(3-Chloro-4-fluoro-phenyl)-(6-methyl-pyrido[3,4-d]pyrimidin-4-yl)-amine Hydrochloride This product was prepared from 6-methyl-pyrido[3,4-d]pyrimid-4-one (1.0 eq.) and 3-chloro-4-fluoro-aniline (1.5 eq.) according to the procedure described for Example 61. The crude product from the filtrate was chromatographed on silica using a gradient of 0% to 10% methanol/methylene chloride to afford the free base of the title product which was converted to the title product as described for Example 60 (47%; M.P. 251–258° C.; LC-MS: 289, 291 (MH+); anal. RP-HPLC:4.18 min.).

EXAMPLE 68
(6-Methyl-pyrido[3,4-d]pyrimidin-4-yl)-(3-trifluoromethyl-phenyl)-amine Hydrochloride This product was prepared from 6-methyl-pyrido[3,4-d]pyrimid-4-one (1.0 eq.) and 3-trifluoromethyl-aniline (1.5 eq.) according to the procedure described for Example 61. The crude product from the filtrate was chromatographed on silica using a gradient of 0% to 5% methanol/methylene chloride to afford the free base of the title product which was converted to the title product as described for Example 60 (33%; M.P. 269–270° C.; LC-MS: 305 (MH+); anal. RP-HPLC:4.30 min.).

EXAMPLE 69
(4-Fluoro-3-methyl-phenyl)-(6-methyl-pyrido[3,4-d]pyrimidin-4-yl)-amine Hydrochloride This product was prepared from 6-methyl-pyrido[3,4-d]pyrimid-4-one (1.0 eq.) and 4-fluoro-3-methyl-aniline (1.5 eq.) according to the procedure described for Example 61. The crude product from the filtrate was chromatographed on silica using 4% methanol/96% methylene chloride to afford the free base of the title product which was converted to the title product as described for Example 60 (41%; M.P. 246–250° C.; LC-MS: 269 (MH+); anal. RP-HPLC: 3.79 min.).

EXAMPLE 70
2-Iodo-4-(6-methyl-pyrido[3,4-d]pyrimidin-4-ylamino)-phenol hydrochloride 6-Methyl-pyrido[3,4-d]pyrimid-4-one (161 mg, 1.00 mmol) was added to polymer-supported triphenylphosphine (1.66 g of about 3 mmol P/g polymer; 5.0 mmol) along with $CCl_4$ (1.54 g, 10.0 mmol) in 1,2-dichloroethane (6 mL). The reaction mixture was heated to 60° C. for 2 hours and then the resin was filtered and washed with 1,2-dichloroethane. The filtrate was collected in a flask containing 4-hydroxy-3-iodo-aniline (0.235 g, 1.00 mmol) and concentrated to 5 mL by evaporation. After 12 hours reflux under nitrogen followed by cooling to 20° C., the title product was collected by filtration (347 mg; 83%; M.P. 261–265° C.; LC-MS: 379 (MH+); anal. RP-HPLC: 3.20 min.).

EXAMPLE 71
(4-Bromo-3-fluoro-phenyl)-(6-methyl-pyrido[3,4-d]pyrimidin-4-yl)-amine Hydrochloride This product was prepared from 6-methyl-pyrido[3,4-d]pyrimid-4-one (1 eq.) and 3-bromo-4-fluoro-aniline (1.0 eq.) and isolated according to the method employed for Example 70 (53%; M.P. 251–254° C.; LC-MS: 333, 335 (MH+); anal. RP-HPLC:4.07 min.).

EXAMPLE 72
4-(6.7-Dimethyl-2,3-dihydro-indol-1-yl)-pyrido[3,4-d]pyrimidine Hydrochloride To 4-chloro-pyrido[3,4-d]pyrimidine (200 mg, 1.21 mmol) in isopropanol (3 mL) was added 6,7-dimethylindoline (211 mg, 1.44 mmol) and pyridine (190 mg, 2.41 mmol). The reaction mixture was heated to reflux under an atmosphere of dry nitrogen for 6 hours. Solvent was removed in vacuo and the residue was dissolved in $CHCl_3$ and washed with saturated aqueous sodium carbonate. The organic phase was dried over sodium sulfate concentrated in vacuo, and flash chromatographed on silica in 45% acetone/hexanes to afford 60 mg of the free base of the title product (LC-MS: 278 (MH+). This material was dissolved in a minimum volume of 10% methanol in methylene chloride and 1 mole equivalent of HCl in ether was added dropwise with stirring. The reaction mixture was diluted with four volumes of ether and the precipitated title product was filtered and dried in vacuo (58 mg; M.P. 248° C.; GC-MS: 277 (M+); anal. RP-HPLC:4.06 min.)

EXAMPLE 73
(3-Ethynyl-phenyl)-pyrido[3,4-d]pyrimidin-4-amine Hydrochloride

To 4-chloro-pyrido[3,4-d]pyrimidine (250 mg, 1.50 mmol) in N-methylpyrrolidin-2-one (0.5 mL) was added 3-ethynylaniline (212 mg, 1.81 mmol) and pyridine (237 mg, 3.0 mmol). The reaction mixture was heated to 80° C. under an atmosphere of dry nitrogen for 3 hours. The reaction mixture was dissolved in $CHCl_3$ and washed with saturated aqueous sodium carbonate, and brine. The organic phase was dried over sodium sulfate, concentrated in vacuo, and flash chromatographed on silica with a gradient of 40% to 70% acetone/hexanes to afford 120 mg of product. This product was dissolved in a minimal amount of $CHCl_3$, titrated with 1 eq. HCl in ether, and dilution with ether. The resultant precipate was filtered and dried in vacuo to yield the yellow title product (133 mg; M.P. 233–235° C.; LC-MS: 247 (MH+); anal. RP-HPLC: 3.45 min.).

EXAMPLE 74
Benzo[b]thiophen-5-yl-pyrido[3,4-d]pyrimidin-4-yl-amine Hydrochloride To 4-chloro-pyrido[3,4]pyrimidine (250 mg, 1.50 mmol) in N-methylpyrrolidin-2-one (0.5 mL) was added benzo[b]thiophen-5-yl-amine (270 mg, 1.81 mmol) and pyridine (237 mg, 3.0 mmol). The reaction mixture was heated to 80° C. under an atmosphere of dry nitrogen for 3 hours. The reaction mixture was dissolved in $CHCl_3$ and washed with saturated aqueous sodium carbonate and brine. The organic phase was dried over sodium sulfate, concentrated in vacuo, and flash chromatographed on silica in 40% acetone/hexanes to afford 180 mg of product. This product was dissolved in a minimal amount of $CHCl_3$, titrated with 1 eq. HCl in ether, and dilution with ether. The resultant precipate was filtered and dried in vacuo to yield the yellow title product (188 mg; M.P. 280–282° C.; LC-MS: 279 (MH+); anal. RP-HPLC: 3.63 min.).

EXAMPLE 75
(3-Ethynyl-phenyl)-(6methyl-pyrido[3,4-d]pyrimidin-4-yl)-amine Hydrochloride This material was prepared from 4-chloro-6-methyl-pyrido[3,4-d]pyrimidine (1.0 eq.) and 3-ethynylaniline (1.1 eq.) as described for Example 74. After extraction chromatography of the residue on silica in 20% to 80% acetone/hexanes afforded 166 mg of the title product as its free-base which was converted to the title product (M.P. 250–252° C.; LC-MS: 261 (MH+); anal.RP-HPLC: 3.69 min.).

EXAMPLE 76
4-(6-Chloro-2,3-dihydro-indol-1-yl)-6-methyl-pyrido[3,4-d]pyrimidine This material was produced from 4-chloro-6-methyl-pyrido[3,4-d]pyrimidine (1.0 eq.) and 6-chloroindoline (1.1 eq.) as described for Example 74. Preparative reversed-phase (C18) chromatography utilizing a gradient of 15% to 70% acetonitrile/pH4.5, 50 mM ammonium acetate followed by lyophilization of the appropriate fractions afforded the title product (30%) (M.P. 232–234° C.; LC-MS: 297 (MH+); anal.RP-HPLC:4.33 min.).

EXAMPLE 77
(1H-Indol-5-yl)-(6-methyl-pyrido[3,4-d]pyrimidin-4-yl)-amine Methanesulfonate This material was produced from 4-chloro-6-methyl-pyrido[3,4-d]pyrimidine (1.0 eq.) and 5-aminoindole (1.1 eq.) as described for Example 74. Preparative reversed-phase (C18) chromatography utilizing a gradient of 15% to 70% acetonitrile/pH4.5, 50 mM ammonium acetate followed by lyophilization of the appropriate fractions afforded free-base (30%) of the title product (M.P. 262–263° C.; LC-MS: 276 (MH+); anal.RP-HPLC: 2.98 min.). This material was converted to the title product by dissolution in a mimimal amount of $CHCl^3$ followed by addition of 1 eq. of methane sulfonic acid. Dilution with ether precipitated the title product which was filtered and dried in vacuo (M.P. 317–318° C.).

EXAMPLE 78
(3-Ethynyl-phenyl)-(5-methylsulfanyl-7H-pyrrolo[2,3-d]pyrimidin-4-yl)-amine To 5-bromo-4-chloro-7H-pyrrolo[2,3-d]pyrimidine (0.18 g, 0.77 mmol) in dry THF (2 ml), cooled in a dry ice-acetone bath, was added dropwise n-butyllithium (0.77 ml, 1.9 mmol, 2.5 M in hexanes). The mixture was stirred for 1 hour, then dimethyldisulfide (0.077 mL, 0.77 mmol) suspended in dry THF (1 ml) was added. The solution was stirred for 2.5 hours at −78° C. and then diluted with aqueous $NH_4Cl$. The phases were separated and the water extracted 2 times with ethyl acetate. The combined organic phases were dried over $Na_2SO_4$, and concentrated in vacuo to afford 4-chloro-5-methylsulfanyl-7H-pyrrolo[2,3-d]pyrimidine as an orange solid (150 mg).

To 4-chloro-5-methylsulfanyl-7H-pyrrolo[2,3-d]pyrimidine (150 mg, 0.75 mmol) in dry methanol (2 ml) was added m-aminophenyl acetylene (110 mg, 0.90 mmol). The solution was heated in a sealed pressure tube at 125° C. for 5.5 hours. The reaction mixture was cooled to ambient temperature, filtered with a small amount of methanol and dried in vacuo to afford the title compound as a tan powder (57 mg, 27%). TS-MS: 281 (MH+); anal. RP18-HPLC RT:4.74 min.

Preparation 1
Pyrido[4,3-d]pyrimidone from 4-aminonicotinic Acids

6-Methyl-4-aminonicotinic acid (420 mg, 2.74 mmol) and dry formamide were heated to 165° C. for 6 hours under $N_2$. The reaction mixture was cooled to room temperature and the formamide was removed in vacuo. The remaining residue was purified by reverse-phase HPLC (linear gradient 5–100% acetonitrile at pH 4.50, 50 mM ammonium acetate over 1 hour with a flow rate of 23.0 mL/min.) to afford the title product (50%; RT=1.48 min.; M+=195).

Preparation 2
6-Methyl-pyrido[3,4-d]pyrimid-4-one

5-Amino-2-methyl-4pyridinecarboxylic acid was prepared according to Palt, K.; Celadnik, M.; Dvorackova, D.; Kubala, E., Cesk. Farm., 32(8), 275–278 (1983). This carboxylic acid was converted to the title product by heating in formamide at 165° C. according to the procedure of Robins, R.; Hitchings, G.; J. Am. Chem. Soc. 77, 2256 (1965).

What is claimed is:
1. A compound of the formula

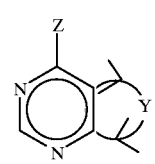

I or a stereoisomer, pharmaceutically acceptable salt or prodrug thereof, wherein Y is —$CR^3$=$CR^3$—$NR^4$—;

Z is $NR^1R^2$ wherein $R^1$ is H and $R^2$ is phenyl substituted by $(R^5)_m$;

each $R^3$ is attached to a carbon atom in Y and is independently selected from
   a. hydrogen,
   b. trifluoromethyl, halo, nitro, hydroxy, amino, cyano, $(C_1-C_4)$alkyl, $(C_1-C_4)$alkoxy, $(C_1-C_4)$alkoxycarbonyl, $(C_1-C_4)$alkanoyloxy, $(C_1-C_4)$alkanoylamino, carboxy, phenoxy, benzoyloxy, carbamoyl, mono-N- or di-N-N-di-$(C_1-C_4)$alkylcarbamoyl, mono-N- or di-N,N-$(C_1-C_4)$alkylamino, mono-N or di-N,N-(hydroxy$(C_2-C_4)$alkyl)amino, mono-N or di-N,N-$((C_1-C_4)$alkoxy$(C_2-C_4)$alkyl)amino, anilino, pyrrolidin-1-yl, piperidin-1-yl, morpholino, piperazin-1-yl, 4-$(C_1-C_4)$alkylpiperazin-1-yl, pyridyl, pyrrolo, imidazolo, thiazolo, benzimidazolo, pyridonyl, $(C_1-C_4)$alkylthio, phenylthio, or such groups substituted on $(C_1-C_4)$alkyl;
   hydroxy$(C_2-C_4)$alkoxy$(C_1-C_4)$alkyl, $(C_1-C_4)$alkoxy-$(C_2-C_4)$alkoxy-$(C_1-C_4)$alkyl, hydroxy$(C_2-C_4)$alkylthio$(C_1-C_4)$alkyl, $(C_1-C_4)$alkoxy$(C_2-C_4)$alkylthio$(C_1-C_4)$alkyl, hydroxyamino, benzoylamino, mono-N or di- N,N-$(C_1-C_4)$alkylcarbamoylmethylamino, carbamoylmethylamino, $(C_1-C_4)$alkoxycarbonylamino, $(C_1-C_4)$alkanoylamino, carboxymethylamino, $(C_1-C_4)$alkoxycarbonylmethylamino, $(C_1-C_4)$alkoxyamino, $(C_2-C_4)$alkanoyloxyamino, phenyl$(C_1-C_4)$alkylamino, $(C_1-C_4)$alkylsulfonylamino, benzenesulfonamido, 3-phenylureido, 2-oxopyrrolidin-1-yl, 2,5-dioxopyrrolidin-1-yl, ureido, $(C_1-C_4)$alkoxy$(C_1-C_4)$alkylcarbonylamino, $(C_1-C_4)$alkylsulfinyl, $(C_1-C_4)$alkylsulfonyl, $(C_1-C_4)$alkoxy$(C_2-C_4)$alkylthio, mono-, di- or trifluoromethyloxy, $(C_1-C_4)$alkylenedioxy, guanidino, aminocarbonyl, mono-N- or di-N,N-$(C_1-C_4)$alkylaminocarbonyl, phenyl$(C_1-C_4)$alkoxy, carboxymethoxy, $(C_1-C_4)$alkoxycarbonylmethoxy, carbamoylmethoxy, mono-N or di-N,N-($C_1$–$C_4$)alkyl carbamoylmethoxy, mono-N- or di-N,N-(hydroxy($C_2$–$C_4$)alkyl)carboxamido, mono-N- or di-N,N-(($C_1$–$C_4$)alkoxy ($C_2$–$C_4$)alkyl)carboxamido or bis(($C_1$–$C_4$)alkanesulfonyl)amido; or C. ($C_2$–$C_4$)alkoxy, ($C_2$–$C_4$)alkylthio, ($C_2$–$C_4$)alkanoyloxy, ($C_2$–$C_4$)alkylamino, ($C_1$–$C_4$)alkyl($C_1$–$C_4$)alkylenedioxy, ($C_2$–$C_4$)alkanoylamino, ($C_2$–$C_4$)alkenyl, or ($C_2$–$C_4$)alkynyl; each such group substituted with amino, halo, hydroxy, ($C_2$–$C_4$)alkanoyloxy, ($C_1$–$C_4$)alkoxy, mono-N- or di-N,N-($C_1$–$C_4$)alkylamino, mono-N or di-N,N-(hydroxy($C_2$–$C_4$)alkyl)amino, mono-N or di-N,N-(($C_1$–$C_4$)alkoxy($C_2$–$C_4$)alkyl)amino, ($C_1$–$C_4$)alkanoylamino, phenoxy, anilino, imidazol-1-yl; phenylthio, piperidino, pyridyl, carboxy($C_1$–$C_4$)alkylthio ($C_s$–$C_4$)alkoxy, morpholino, piperazin-1-yl-, 4-($C_1$–$C_4$)alkylpiperazin-1-yl-, carboxy, ($C_1$–$C_4$)alkoxycarbonyl, carbamoyl, mono-N- or di-N,N-($C_1$–$C_4$)alkylcarbamoyl, mono-N- or di-N,N-($C_1$–$C_4$)alkylcarboxamido or mono-N- or di-N,N-(hydroxy($C_2$–$C_4$)alkyl)carboxamido; and any phenyl in an $R^3$ substituent is optionally mono- or di-substituted with halo, nitro, trifluoromethyl, hydroxy, ($C_1$–$C_4$)alkoxy, ($C_1$–$C_4$)alkyl, amino, mono-N-alkylamino, or N,N-dialkylamino;

$R^4$ is hydrogen, ($C_1$–$C_4$)alkyl, arylsulfonyl, allyl; or a ($C_2$–$C_4$)alkyl group substituted with ($C_1$–$C_4$)alkoxy;

each $R^5$ is independently selected from mono-, di- or tri-fluoromethyl, halo, nitro, hydroxy, amino, azido, isothiocyano, ($C_1$–$C_4$)alkyl, phenyl, thienyl, ($C_1$–$C_4$)alkoxy, benzyloxy, phenoxy, ($C_2$–$C_6$)alkenyl, ($C_2$–$C_6$)alkynyl, ($C_1$–$C_4$)alkylenedioxy, cyano, benzoylamino, trifluoromethylcarbonylamino, ($C_1$–$C_4$)alkanoylamino, ($C_1$–$C_4$)alkanoyl, N-mono- or N,N-di-($C_1$–$C_4$)alkylamino, ($C_1$–$C_4$)alkylsulfonylamino, trifluoromethylsulfonylamino, ($C_1$–$C_4$)alkylthio, ($C_1$–$C_4$)alkylsulfinyl or ($C_1$–$C_4$)alkylsulfonyl, pyrrol-1-yl, piperidin-1-yl or pyrrolidin-1-yl, said phenyl, benzyloxy, phenoxy and benzoylamino optionally mono-substituted with halo, nitro, trifluoromethyl, hydroxy or ($C_1$–$C_4$)alkyl and said ($C_1$–$C_4$)alkylenedioxy is linked at both ends to adjacent carbons on the benzene moiety; wherein at least one $R^5$ is 3-ethynyl;

each $R^6$ is independently selected from hydroxy, amino, N-mono- or N,N-di-($C_1$–$C_4$)alkylamino, sulfo, or ($C_1$–$C_4$)alkoxy (provided that such groups are not attached to a ring carbon which is directly adjacent to the ring N-), or $R^6$ for each occurrence is independently carboxy, hydroxy($C_1$–$C_4$)alkyl, ($C_1$–$C_4$)alkoxy($C_1$–$C_4$)alkyl, amino($C_1$–$C_4$)alkyl, mono-N- or di-N,N-($C_1$–$C_4$)alkylamino($C_1$ –$C_4$)alkyl, morpholino ($C_1$–$C_4$)alkyl, 4-($C_1$–$C_4$)alkyl-piperazin-1-yl($C_1$–$C_4$)alkyl, carboxy ($C_1$–$C_4$)alkyl, ($C_1$–$C_4$)alkoxycarbonyl, sulfo($C_1$–$C_4$)alkyl, pyridyl($C_1$–$C_4$)alkyl or ($C_1$–$C_4$)alkyl; and m is an integer from 1 to 3.

2. The compound of claim 1 wherein each $R^3$ is independently selected from hydrogen, hydroxy, ($C_1$–$C_4$)alkoxy, hydroxy($C_2$–$C_4$)alkoxy, amino($C_2$–$C_4$)alkyl, amino($C_2$–$C_4$)alkoxy, ($C_1$–$C_4$)alkoxy($C_2$–$C_4$)alkoxy, hydroxy($C_1$–$C_4$)alkyl($C_1$–$C_4$)alkylenedioxy, ($C_1$–$C_4$)alkoxy($C_1$–$C_4$)alkyl ($C_1$–$C_4$)alkylenedioxy, mono-N- or di-N,N-($C_1$–$C_4$)alkylamino($C_2$–$C_4$)alkoxy, carboxy($C_1$–$C_4$)alkoxy, morpholino($C_2$–$C_4$)alkoxy, imidazol-1-yl($C_2$–$C_4$)alkoxy, 4($C_1$–$C_4$)alkylpiperazin-1-yl-($C_2$–$C_4$)alkoxy, ($C_1$–$C_4$)alkoxy($C_2$–$C_4$)alkanoyloxy, nitro, hydroxyamino, amino, pyridyl, pyrrolo, imidazolo, thiazolo, benzimidazolo, pyridenyl, mono-N- or di-N,N-($C_1$–$C_4$)alkylamino, ($C_1$–$C_4$)alkanoylamino, hydroxy($C_2$–$C_4$)alkylamino, ($C_1$–$C_4$)alkoxy($C_2$–$C_4$)alkylamino, ($C_1$–$C_4$)alkylsulfonamido, morpholino, ($C_1$–$C_4$)alkyl-piperazin-1-yl, bis(($C_1$–$C_4$)alkanesulfonyl) amido, di-N,N-($C_1$–$C_4$)alkylamino($C_2$–$C_4$)alkylamino, ($C_1$–$C_4$)alkylamino($C_2$–$C_4$)alkylamino, piperidin-1-yl, , pyrrolidin-1-yl, ($C_1$–$C_4$)alkoxy($C_1$–$C_4$)alkylcarbonylamino, carboxy, ($C_1$–$C_4$)alkoxycarbonyl, ($C_1$–$C_4$)alkoxycarbonyl ($C_1$–$C_4$)alkoxy, amido, mono-N- or di-N,N-($C_1$–$C_4$)alkylaminocarbonyl, mono-N- or di-N,N-(hydroxy($C_2$–$C_4$)alkyl)aminocarbonyl, ($C_1$–$C_4$)alkyl, hydroxy($C_1$–$C_4$)alkyl, mono-N- or di-N,N-(($C_1$–$C_4$)alkoxy($C_1$–$C_4$)alkyl)amino ($C_1$–$C_4$)alkyl, mono-N- or di-N,N-($C_1$–$C_4$)alkylamino($C_1$–$C_4$)alkyl, ($C_1$–$C_4$)alkanoylamino($C_1$–$C_4$)alkyl, ($C_1$–$C_4$)alkoxy($C_2$–$C_4$)alkoxy($C_1$–$C_4$)alkyl, ($C_1$–$C_4$)alkylthio, ($C_1$–$C_4$)alkoxy($C_2$–$C_4$)alkylthio or hydroxy($C_2$–$C_4$)alkylthio.

3. The compound of claim 1 selected from the group consisting of:

(3-ethynyl-phenyl)-(7H-pyrrolo[2,3-d]pyrimidin-4-yl)-amine hydrochloride;

(7-benzenesulfonyl-7H-pyrrolo[2,3-d]pyrimidin-4-yl)-(3-ethynyl-phenyl)-amine;

(3-ethynyl-phenyl)-[7-(2-morpholin-4-yl-ethyl)-7H-pyrrolo[2,3-d]pyrimidin-4-yl]-amino;

(3-ethynyl-phenyl)-[7-(2-methoxy-ethyl)-7H-pyrrolo[2,3-d]pyrimidin-4-yl]-amine;

(7-allyl-pyrrolo[2,3-d]pyrimidin-4-yl)-(3-ethynyl-phenyl)-amine hydrochloride;

(3-ethynyl-phenyl)-(7-methyl-pyrrolo[2,3-d]pyrimidin-4-yl)-amine hydrochloride;

(5-bromo-7H-pyrrolo[2,3-d]pyrimidin-4-yl)-(3-ethynyl-phenyl)-amine;

(3-ethynyl-phenyl)-(5-iodo-7H-pyrrolo[2,3-d]pyrimidin-4-yl)-amine;

4-(3-ethynyl-phenylamino)-7H-pyrrolo[2,3-d]pyrimidine-5-carboxylic acid;

(3-ethynyl-phenyl)-(5-methyl-7H-pyrrolo[2,3-d]pyrimidin-4-yl)-amine hydrochloride;

4-(3-ethynyl-phenylamino)-7H-pyrrolo[2,3-d]pyrimidine-5-carboxylic acid methyl ester hydrochloride;

(3-ethynyl-phenyl) (S-methylsulfanyl-7H-pyrrolo[2,3-d]pyrimidin-4-yl) amine; and 4-(3-ethynyl-phenylamino)-7H-pyrrolo[2,3-d]pyrimidine-5-carbonitrile.

4. A pharmaceutical composition which comprises a compound of claim 1 and a pharmaceutically acceptable carrier.

5. A method of treating hyperproliferative disorders resulting from erbB protein tyrosine kinase activity which comprises administering to a mammal in need of such treatment an effective amount of a compound of claim 1.

6. A method as recited in claim 5 wherein the hyperproliferative disease is cancer.

7. A method as recited in claim 6 wherein the disease is brain, lung, squamous cell, bladder, gastric, pancreatic, hepatic, renal, colorectal, breast, head, prostate, neck, oesophageal, gynecological or thyroid cancer.

8. A method as recited in claim 5 wherein the hyperproliferative disorder is noncancerous.

9. A method as recited in claim 8 wherein the noncancerous hyperproliferative disorder is psoriasis or benign prostatic hyperplasia.

* * * * *